(12) United States Patent  
Barnhill et al.

(10) Patent No.: US 7,698,770 B2
(45) Date of Patent: Apr. 20, 2010

(54) AUTOMATED APPENDAGE CLEANING APPARATUS WITH BRUSH

(75) Inventors: Paul R. Barnhill, Aurora, CO (US); James Glenn, Denver, CO (US); Timothy Prodanovich, Boulder, CO (US)

(73) Assignee: Resurgent Health & Medical, LLC, Golden, CO (US)

( * ) Notice: Subject to any disclaimer, the term of this patent is extended or adjusted under 35 U.S.C. 154(b) by 0 days.

(21) Appl. No.: 11/689,582

(22) Filed: Mar. 22, 2007

(65) Prior Publication Data

US 2008/0099043 A1 May 1, 2008

Related U.S. Application Data

(63) Continuation-in-part of application No. 11/617,177, filed on Dec. 28, 2006.

(60) Provisional application No. 60/863,753, filed on Oct. 31, 2006.

(51) Int. Cl.
*A47L 25/00* (2006.01)
*A47K 7/04* (2006.01)
*A46B 13/04* (2006.01)

(52) U.S. Cl. ............ 15/21.1; 15/88.1; 15/88.2; 15/88.3; 15/97.1; 340/573.1; 4/619; 4/628

(58) Field of Classification Search ............ 15/21.1, 15/88.4, 97.1, 88.1, 88.2, 88.3; 340/573.1; 134/180, 95.2, 181; 4/619, 628

See application file for complete search history.

(56) References Cited

U.S. PATENT DOCUMENTS

| | | | |
|---|---|---|---|
| 2,325,008 A | 7/1943 | Gruett | |
| 2,386,455 A | 10/1945 | Green | |
| 2,522,928 A | 9/1950 | Carroll | |
| 2,647,801 A | 8/1953 | Lycan | |
| 2,769,547 A | 11/1956 | Hirsch | |
| 2,826,763 A | 3/1958 | Bass | |
| 3,059,815 A | 10/1962 | Parsons, Jr. | |
| 3,081,471 A | 3/1963 | Newell | |
| 3,220,424 A | 11/1965 | Nelson | |
| 3,243,264 A | 3/1966 | Hickey | |
| 3,437,274 A | 4/1969 | Apri | |

(Continued)

FOREIGN PATENT DOCUMENTS

DE 19903079 8/2000

(Continued)

OTHER PUBLICATIONS

International Search Report for counterpart International (PCT) Patent Application No. PCT/US2007/088690, mailed Jun. 10, 2008, pp. 1-2.

(Continued)

*Primary Examiner*—Gary K Graham
(74) *Attorney, Agent, or Firm*—Sheridan Ross P.C.

(57) ABSTRACT

A system is provided for providing automated washing for debris removal from the skin of a user's hands. At least some embodiments of the present include a friction enhancing structure such as a brush. In at least one embodiment of the invention, the system includes an RFID capability for identifying when at least one component, such as a removable brush, is due to for replacement for sanitation reasons.

13 Claims, 17 Drawing Sheets

U.S. PATENT DOCUMENTS

| | | |
|---|---|---|
| 3,529,774 A | 9/1970 | Apri |
| 3,639,844 A | 2/1972 | Karklys |
| 3,647,147 A | 3/1972 | Cook |
| 3,699,984 A | 10/1972 | Davis |
| 3,744,149 A | 7/1973 | Helbling |
| 3,754,559 A | 8/1973 | Seiwert |
| 3,757,806 A | 9/1973 | Baaskar et al. |
| 3,817,651 A | 6/1974 | Law et al. |
| 3,844,278 A | 10/1974 | Weider |
| 3,881,328 A | 5/1975 | Kleimola et al. |
| 3,918,117 A | 11/1975 | Plante |
| 3,918,987 A | 11/1975 | Kopfer |
| 3,967,478 A | 7/1976 | Guinn |
| 3,992,730 A | 11/1976 | Davis |
| 3,997,873 A | 12/1976 | Thornton |
| 4,001,599 A | 1/1977 | Karklys |
| 4,020,856 A | 5/1977 | Masterson |
| 4,073,301 A | 2/1978 | Mackinnon |
| 4,120,180 A | 10/1978 | Jedora |
| 4,137,929 A | 2/1979 | Grossman |
| 4,219,367 A | 8/1980 | Cary, Jr. et al. |
| 4,275,385 A | 6/1981 | White |
| 4,295,233 A | 10/1981 | Hinkel et al. |
| 4,398,310 A | 8/1983 | Lienhard |
| 4,402,331 A | 9/1983 | Taldo et al. |
| 4,453,286 A | 6/1984 | Wieland |
| 4,496,519 A | 1/1985 | McGuire |
| 4,509,543 A | 4/1985 | Livingston et al. |
| 4,601,064 A | 7/1986 | Shipley |
| 4,606,085 A | 8/1986 | Davies |
| 4,606,500 A | 8/1986 | Mussler et al. |
| 4,670,010 A | 6/1987 | Dragone |
| 4,688,585 A | 8/1987 | Vetter |
| 4,769,863 A | 9/1988 | Tegg et al. |
| 4,817,651 A | 4/1989 | Crisp et al. |
| 4,896,144 A | 1/1990 | Bogstad |
| 4,916,435 A | 4/1990 | Fuller |
| 4,921,211 A | 5/1990 | Novak et al. |
| 4,925,495 A | 5/1990 | Crisp et al. |
| 4,942,631 A | 7/1990 | Rosa |
| 4,999,613 A | 3/1991 | Williamson et al. |
| 5,016,172 A | 5/1991 | Dessertine |
| 5,031,258 A | 7/1991 | Shaw |
| 5,060,323 A | 10/1991 | Shaw |
| 5,074,322 A | 12/1991 | Jaw |
| RE33,810 E | 2/1992 | Strieter |
| 5,086,526 A | 2/1992 | Van Marcke |
| 5,119,104 A | 6/1992 | Heller |
| 5,184,642 A | 2/1993 | Powell |
| 5,193,563 A | 3/1993 | Melech |
| 5,199,118 A | 4/1993 | Cole et al. |
| 5,202,666 A | 4/1993 | Knippscheer |
| 5,238,749 A | 8/1993 | Cueman et al. |
| 5,257,423 A | 11/1993 | Jacobsen et al. |
| 5,265,628 A | 11/1993 | Sage et al. |
| 5,291,399 A | 3/1994 | Chaco |
| 5,340,581 A | 8/1994 | Tseng et al. |
| 5,387,993 A | 2/1995 | Heller et al. |
| RE35,035 E | 9/1995 | Shipley |
| 5,455,851 A | 10/1995 | Chaco et al. |
| 5,465,082 A | 11/1995 | Chaco |
| 5,503,840 A | 4/1996 | Jacobson et al. |
| 5,515,426 A | 5/1996 | Yacenda et al. |
| 5,548,637 A | 8/1996 | Heller et al. |
| 5,561,412 A | 10/1996 | Novak et al. |
| 5,572,195 A | 11/1996 | Heller et al. |
| 5,594,786 A | 1/1997 | Chaco et al. |
| 5,601,100 A | 2/1997 | Kawakami et al. |
| 5,610,589 A | 3/1997 | Evans et al. |
| 5,633,742 A | 5/1997 | Shipley |
| 5,670,945 A | 9/1997 | Applonie |
| 5,689,229 A | 11/1997 | Chaco et al. |
| 5,695,091 A | 12/1997 | Winings et al. |
| 5,699,038 A | 12/1997 | Ulrich et al. |
| 5,702,115 A | 12/1997 | Pool |
| 5,727,579 A | 3/1998 | Chardack |
| 5,745,272 A | 4/1998 | Shipley |
| 5,765,242 A | 6/1998 | Marciano |
| 5,774,865 A | 6/1998 | Glynn |
| 5,781,942 A | 7/1998 | Allen et al. |
| 5,793,653 A | 8/1998 | Segal |
| 5,808,553 A | 9/1998 | Cunningham |
| 5,812,059 A | 9/1998 | Shaw et al. |
| 5,818,617 A | 10/1998 | Shipley |
| 5,822,418 A | 10/1998 | Yacenda et al. |
| 5,822,544 A | 10/1998 | Chaco et al. |
| 5,823,447 A | 10/1998 | Maybach |
| 5,838,223 A | 11/1998 | Gallant et al. |
| 5,845,225 A | 12/1998 | Mosher |
| 5,860,437 A | 1/1999 | Fernie |
| 5,863,497 A | 1/1999 | Dirksing |
| 5,870,015 A | 2/1999 | Hinkel |
| 5,900,067 A | 5/1999 | Jones |
| 5,900,801 A | 5/1999 | Heagle et al. |
| 5,924,148 A | 7/1999 | Flowers, Sr. |
| 5,939,974 A | 8/1999 | Heagle et al. |
| 5,945,068 A | 8/1999 | Ferone |
| 5,945,910 A | 8/1999 | Gorra |
| 5,952,924 A | 9/1999 | Evans et al. |
| 5,954,069 A | 9/1999 | Foster |
| 5,966,573 A | 10/1999 | Yu et al. |
| 5,966,753 A | 10/1999 | Gauthier et al. |
| 5,972,126 A | 10/1999 | Fernie |
| 5,979,500 A | 11/1999 | Jahrling et al. |
| 5,992,430 A | 11/1999 | Chardack et al. |
| 6,029,600 A | 2/2000 | Davis |
| 6,031,461 A | 2/2000 | Lynn |
| 6,037,871 A | 3/2000 | Babylon |
| 6,038,331 A | 3/2000 | Johnson |
| 6,038,519 A | 3/2000 | Gauthier et al. |
| 6,110,292 A | 8/2000 | Jewett et al. |
| 6,125,482 A | 10/2000 | Foster |
| 6,131,587 A | 10/2000 | Chardack et al. |
| 6,147,607 A | 11/2000 | Lynn |
| 6,161,227 A | 12/2000 | Bargenquast |
| 6,176,941 B1 | 1/2001 | Jewett et al. |
| 6,195,588 B1 | 2/2001 | Gauthier et al. |
| 6,211,788 B1 | 4/2001 | Lynn et al. |
| 6,232,870 B1 | 5/2001 | Garber et al. |
| 6,235,351 B1 | 5/2001 | DiMarzio et al. |
| 6,236,317 B1 | 5/2001 | Cohen et al. |
| 6,236,953 B1 | 5/2001 | Segal |
| 6,268,797 B1 | 7/2001 | Berube et al. |
| 6,278,372 B1 | 8/2001 | Velasco, Jr. et al. |
| 6,317,717 B1 | 11/2001 | Lindsey et al. |
| 6,335,686 B1 | 1/2002 | Goff et al. |
| 6,344,794 B1 | 2/2002 | Ulrich et al. |
| 6,351,866 B1 | 3/2002 | Bragulla |
| 6,392,546 B1 | 5/2002 | Smith |
| 6,399,853 B1 | 6/2002 | Roe et al. |
| 6,404,837 B1 | 6/2002 | Thompson et al. |
| 6,413,921 B1 | 7/2002 | Childers et al. |
| 6,417,773 B1 | 7/2002 | Vlahos et al. |
| 6,424,262 B2 | 7/2002 | Garber et al. |
| 6,426,701 B1 | 7/2002 | Levy et al. |
| 6,431,189 B1 | 8/2002 | Deibert |
| 6,448,886 B2 | 9/2002 | Garber et al. |
| 6,462,656 B2 | 10/2002 | Ulrich et al. |
| 6,486,780 B1 | 11/2002 | Garber et al. |
| 6,523,193 B2 | 2/2003 | Saraya |
| 6,524,390 B1 | 2/2003 | Jones |
| 6,539,393 B1 | 3/2003 | Kabala |
| 6,542,568 B1 | 4/2003 | Howes, Jr. et al. |
| 6,577,240 B2 | 6/2003 | Armstrong |

| | | |
|---|---|---|
| 6,600,420 B2 | 7/2003 | Goff et al. |
| 6,663,719 B2 | 12/2003 | Shinozaki et al. |
| 6,671,890 B2 | 1/2004 | Nishioka |
| 6,706,243 B1 | 3/2004 | Sias et al. |
| 6,707,873 B2 | 3/2004 | Thompson et al. |
| 6,727,818 B1 | 4/2004 | Wildman et al. |
| 6,733,595 B1 | 5/2004 | Grillo |
| 6,759,959 B2 | 7/2004 | Wildman |
| 6,768,419 B2 | 7/2004 | Garber et al. |
| 6,825,763 B2 | 11/2004 | Ulrich et al. |
| 6,832,916 B2 | 12/2004 | Collopy |
| 6,882,278 B2 | 4/2005 | Winings et al. |
| 6,883,563 B2 | 4/2005 | Smith |
| 6,892,143 B2 | 5/2005 | Howes, Jr. et al. |
| 6,902,397 B2 | 6/2005 | Farrell et al. |
| 6,938,282 B2 | 9/2005 | Yamamoto |
| 6,956,498 B1 | 10/2005 | Gauthier et al. |
| 6,970,574 B1 | 11/2005 | Johnson |
| D512,648 S | 12/2005 | Smith et al. |
| 6,975,231 B2 | 12/2005 | Lane et al. |
| 6,992,561 B2 | 1/2006 | Sandt et al. |
| 7,010,369 B2 | 3/2006 | Borders et al. |
| 7,015,816 B2 | 3/2006 | Wildman et al. |
| 7,020,508 B2 | 3/2006 | Stivoric et al. |
| 7,080,061 B2 | 7/2006 | Kabala |
| 7,107,631 B2 | 9/2006 | Lang et al. |
| 7,113,094 B2 | 9/2006 | Garber et al. |
| 7,119,688 B2 | 10/2006 | Wildman |
| 7,120,800 B2 | 10/2006 | Ginter et al. |
| 7,123,151 B2 | 10/2006 | Garber et al. |
| 7,150,293 B2 | 12/2006 | Jonte |
| 7,174,577 B2 | 2/2007 | Jost et al. |
| 7,242,306 B2 | 7/2007 | Wildman et al. |
| 7,242,307 B1 | 7/2007 | LeBlond et al. |
| 7,248,933 B2 | 7/2007 | Wildman |
| 7,270,268 B2 | 9/2007 | Garber et al. |
| 7,423,533 B1 | 9/2008 | LeBlond et al. |
| 7,443,305 B2 | 10/2008 | Verdiramo |
| 2002/0019709 A1 | 2/2002 | Segal |
| 2002/0104083 A1 | 8/2002 | Hendricks et al. |
| 2002/0135486 A1 | 9/2002 | Brohagen et al. |
| 2002/0175182 A1 | 11/2002 | Matthews |
| 2003/0069815 A1 | 4/2003 | Eisenberg et al. |
| 2003/0089771 A1 | 5/2003 | Cybulski et al. |
| 2003/0197122 A1 | 10/2003 | Faiola et al. |
| 2004/0083547 A1 | 5/2004 | Mercier |
| 2004/0133081 A1 | 7/2004 | Teller et al. |
| 2004/0150527 A1 | 8/2004 | Harper et al. |
| 2004/0255409 A1 | 12/2004 | Hilscher et al. |
| 2005/0134465 A1 | 6/2005 | Rice et al. |
| 2005/0136949 A1 | 6/2005 | Barnes |
| 2005/0139239 A1 | 6/2005 | Prae |
| 2005/0147526 A1 | 7/2005 | Hishida |
| 2005/0151641 A1 | 7/2005 | Ulrich et al. |
| 2005/0171634 A1 | 8/2005 | York et al. |
| 2005/0248461 A1 | 11/2005 | Lane et al. |
| 2006/0122474 A1 | 6/2006 | Teller et al. |
| 2006/0132316 A1 | 6/2006 | Wildman et al. |
| 2006/0214788 A1 | 9/2006 | Ku et al. |
| 2006/0224051 A1 | 10/2006 | Teller et al. |
| 2006/0229891 A1 | 10/2006 | Grier |
| 2006/0231568 A1 | 10/2006 | Lynn et al. |
| 2006/0241396 A1 | 10/2006 | Fabian et al. |
| 2006/0264730 A1 | 11/2006 | Stivoric et al. |
| 2007/0008146 A1 | 1/2007 | Taylor et al. |
| 2007/0011893 A1 | 1/2007 | Garber et al. |
| 2007/0020212 A1 | 1/2007 | Bernal et al. |
| 2007/0247316 A1 | 10/2007 | Wildman et al. |
| 2007/0257803 A1 | 11/2007 | Munro et al. |
| 2007/0273525 A1 | 11/2007 | Garber et al. |
| 2008/0001763 A1 | 1/2008 | Raja et al. |
| 2008/0031838 A1 | 2/2008 | Bolling |

FOREIGN PATENT DOCUMENTS

| | | |
|---|---|---|
| EP | 0396039 | 11/1990 |
| EP | 0616658 | 9/1994 |
| EP | 0758702 | 2/1997 |
| EP | 1872802 | 1/2008 |
| EP | 1935515 | 6/2008 |
| FR | 2659217 | 9/1991 |
| GB | 2324397 | 10/1998 |
| JP | 5-329065 | 12/1993 |
| WO | WO 80/01983 | 10/1980 |
| WO | WO 93/10311 | 5/1993 |
| WO | WO 03/086274 | 10/2003 |

OTHER PUBLICATIONS

Written Opinion for counterpart International (PCT) Patent Application No. PCT/US2007/088690, mailed Jun. 10, 2008, pp. 1-6.
U.S. Appl. No. 11/617,024, filed Dec. 28, 2006, Prodanovich.
U.S. Appl. No. 11/617,177, filed Dec. 28, 2006, Glenn.
U.S. Appl. No. 11/829,764, filed Jul. 27, 2007, Barnhill.
U.S. Appl. No. 11/829,769, filed Jul. 27, 2007, Barnhill.
U.S. Appl. No. 11/829,775, filed Jul. 27, 2007, Barnhill.
U.S. Appl. No. 11/829,781, filed Jul. 27, 2007, Barnhill.
U.S. Appl. No. 11/829,783, filed Jul. 27, 2007, Barnhill.
U.S. Appl. No. 11/852,099, filed Sep. 7, 2007, Glenn.
"Case Study: FL hospital used IT to monitor hand washing", FierceHealthIT website, dated Aug. 3, 2009, available at http://www.fiercehealthit.com/node/8503/print, printed on Aug. 11, 2009, p. 1.
"Michigan IT Companies Helping the University of Miami Center for Patient Safety Tackle a Leading Cause of Death Using an RTLS Solution to Monitor Staff Hand-Washing Compliance", prnewswire website, dated Jul. 29, 2009, available at http://news.prnewswire.com/DisplayReleaseContext.aspx?ACCT=104&STORY=/www/story/07-29-2009/0005068398&EDATE, printed on Aug. 10, 2009, pp. 1-2.
"HyGreen The Intelligent Hand Hygiene Solution", Xhale, Inc., date unknown, 2 pages.
"HyGreen: How it Works", available at http://www.xhale.com/hygreen/solution/How.asp, printed Jul. 14, 2009, pp. 1-2.
"HyGreen: Sample Reporting", available at http://www.xhale.com/hygreen/solution/Reporting.asp, printed Jul. 14, 2009, pp. 1-3.
International Preliminary Report on Patentability for International (PCT) Patent Application No. PCT/US2007/088690, mailed Jul. 9, 2009.
"HandGiene" available at http://handgienecorp.com/index.jsp, printed Nov. 2, 2009, pp. 1-2.
"Case Study: FL hospital used IT to monitor hand washing", FierceHealthIT website, dated Aug. 3, 2009, available at http://www.fiercehealthit.com/node/8503/print, printed on Aug. 11, 2009, p. 1.
U.S. Appl. No. 12/432,693, Barnhill, (Apr. 29, 2009).
U.S. Appl. No. 12/432,698, Barnhill et al., (Apr. 29, 2009).
U.S. Appl. No. 12/432,711, Glenn et al., (Apr. 29, 2009).
U.S. Appl. No. 12/432,716, Barnhill et al., (Apr. 29, 2009).
U.S. Appl. No. 12/432,718, Barnhill et al., (Apr. 29, 2009).

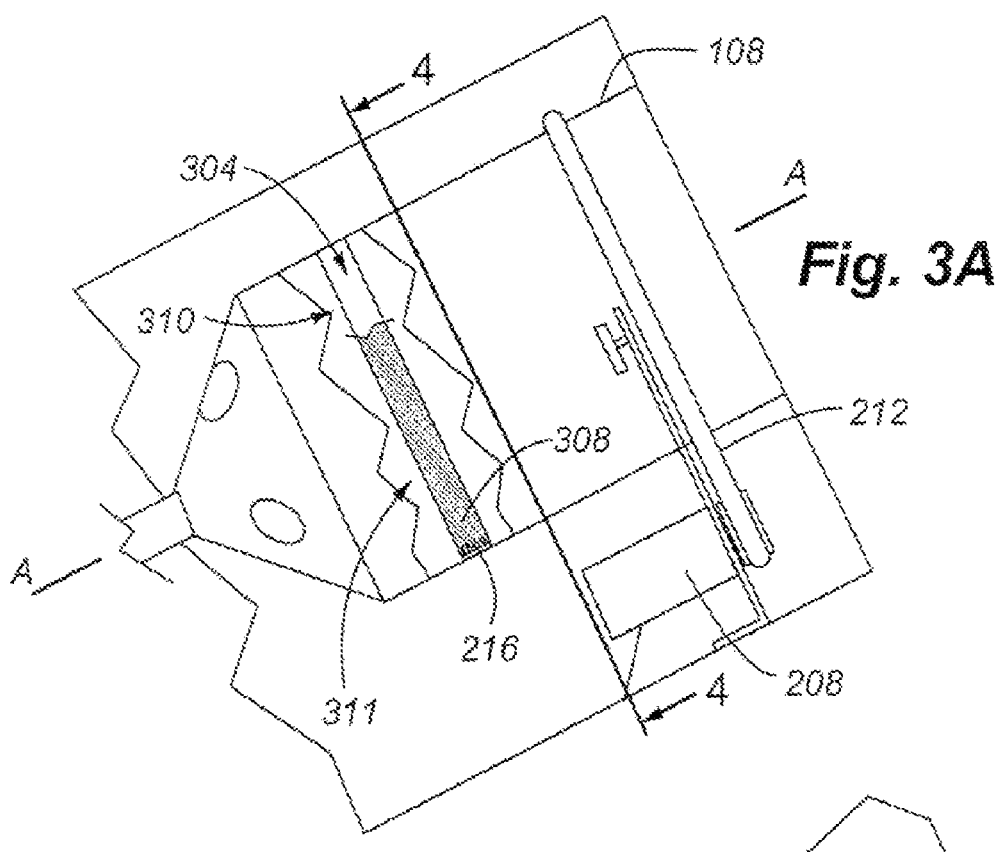
*Fig. 3A*
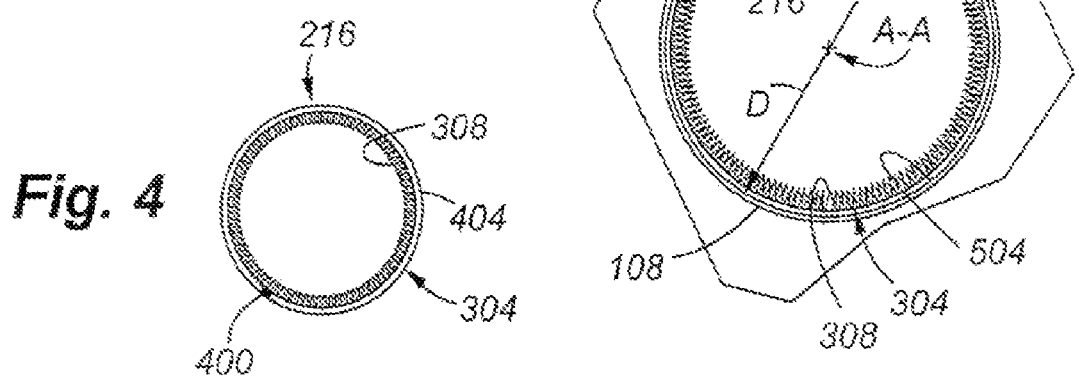
*Fig. 5*
*Fig. 4*
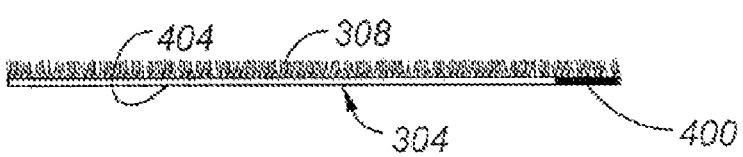
*Fig. 6*
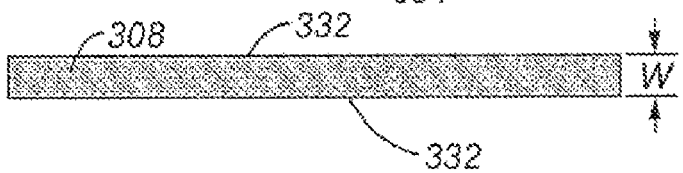
*Fig. 7*

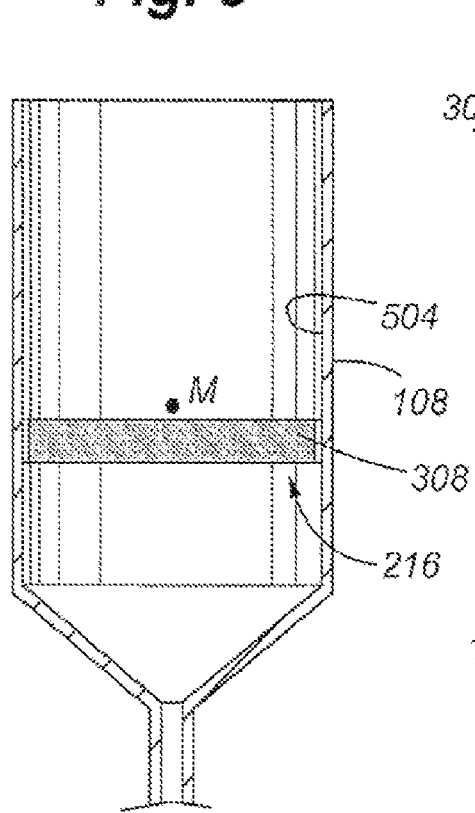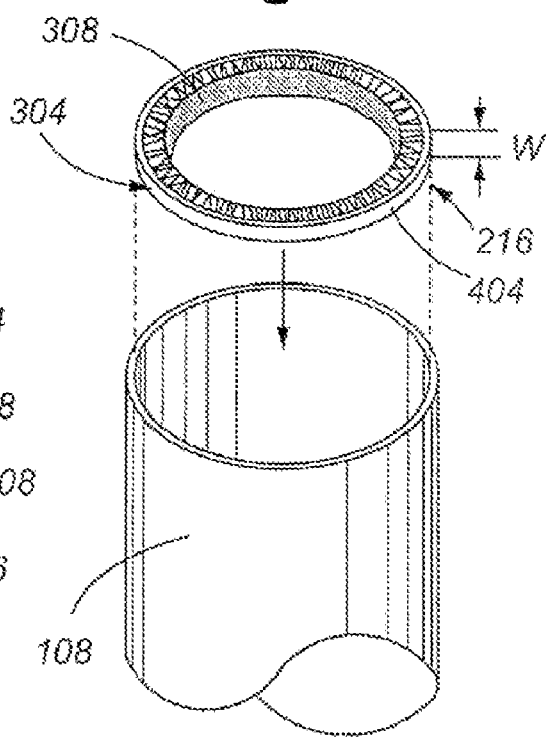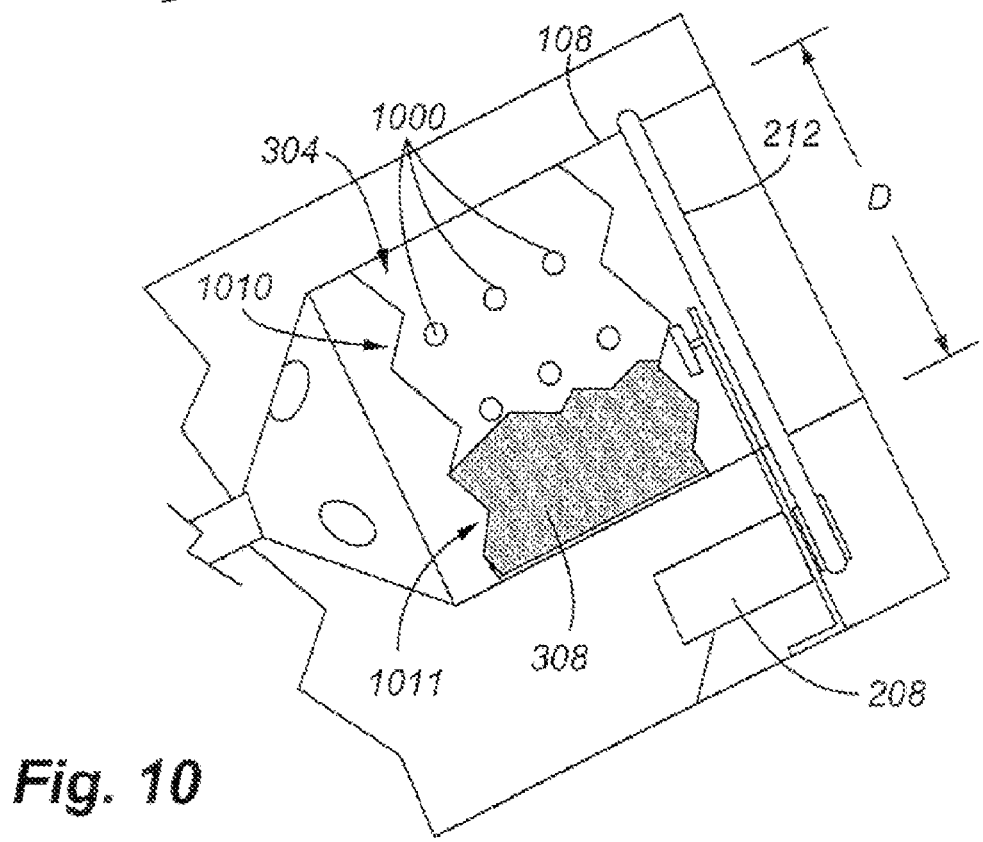

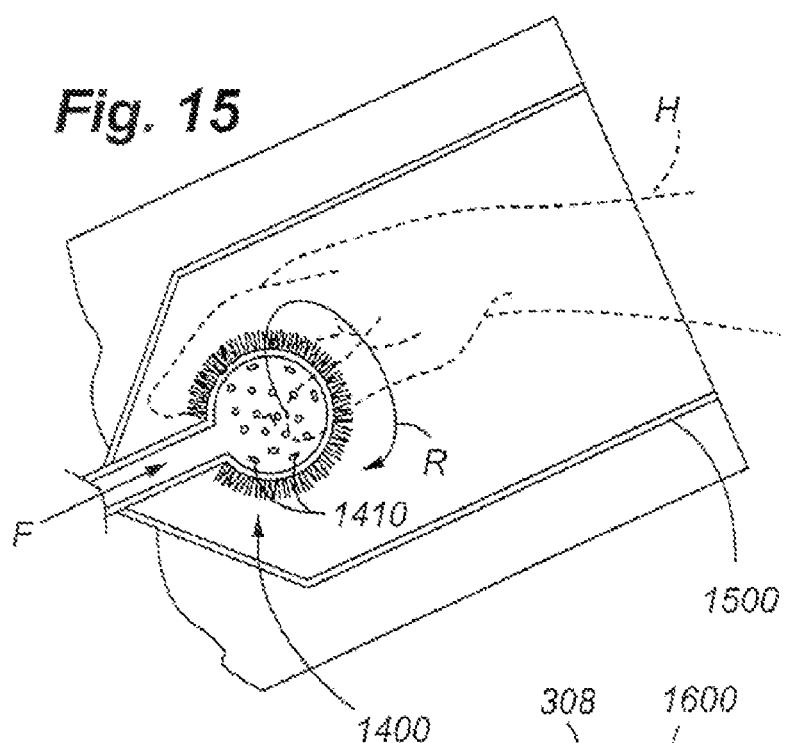
Fig. 15
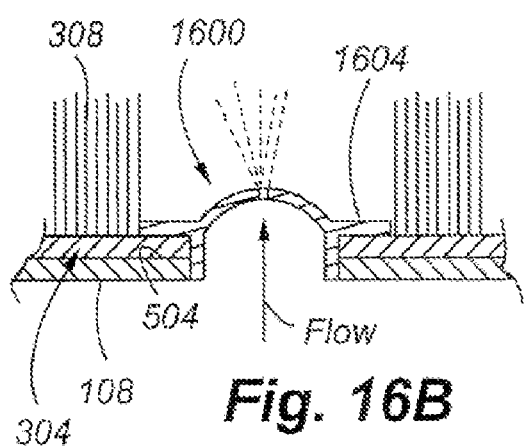
Fig. 16A
Fig. 16B
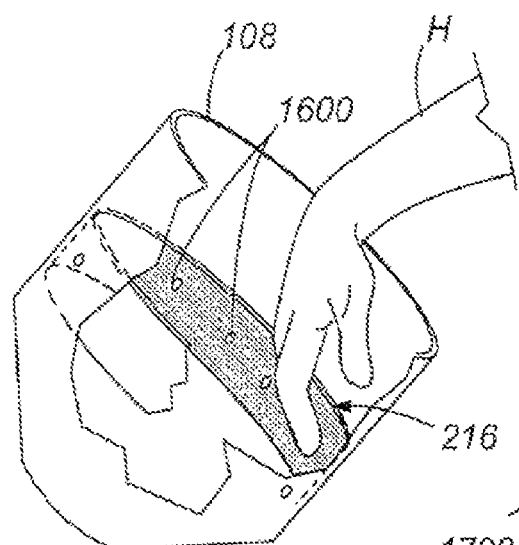
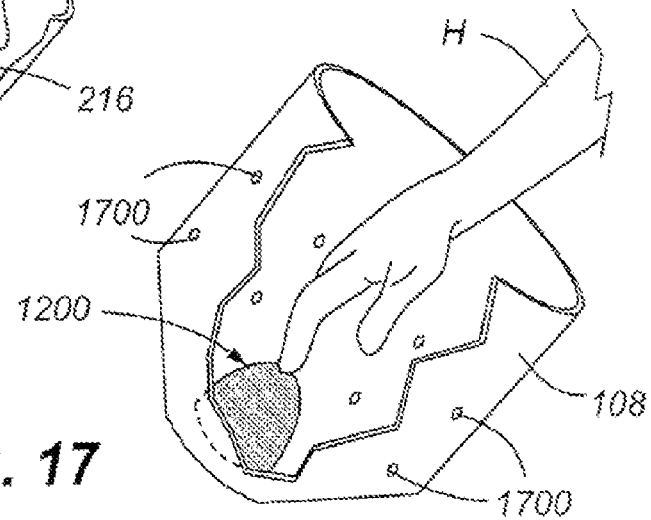
Fig. 17

*Fig. 25*

CLEANING STATION-USE RECORD 2436

| EMPLOYEE NAME | TIME STAMP | DURATION | DATE | BRUSH STATUS ACCEPTABLE | COMPLIANCE |
|---|---|---|---|---|---|
| Janet Smith | 08:00:00 a.m. | 0 secs | 5/21/2006 | N | N |
| Bill Powers | 09:00:23 a.m. | 10 secs | 5/21/2006 | Y | Y |
| Jason Williams | 10:07:40 a.m. | 12 secs | 5/21/2006 | Y | Y |
| Judy Jones | 11:10:05 a.m. | 11 secs | 5/21/2006 | Y | Y |
| Sandra Collins | 11:20:31 a.m. | 11 secs | 5/21/2006 | Y | Y |

BRUSH REPLACEMENT RECORD 2440

| CLEANING STATION DESIGNATION | DATE | PROPER BRUSH COMPLIANCE |
|---|---|---|
| A | 5/22/2006 | N |
| B | 5/22/2006 | Y |
| A | 5/23/2006 | Y |
| B | 5/23/2006 | Y |
| A | 5/24/2006 | Y |
| B | 5/24/2006 | Y |

*Fig. 26*

COMPLIANCE REPORT 2740

| EMPLOYEE NAME | TIME | DATE | STATION DESIGNATION | BRUSHES OK | FULL CYCLE |
|---|---|---|---|---|---|
| Janet Smith | 8:00 a.m. | 5/21/2006 | A | N | N |
| Bill Powers | 9:00 a.m. | 5/21/2006 | A | Y | N |
| Bill Forbes | 10:00 a.m. | 5/21/2006 | B | Y | N |
| Jason Williams | 10:07 a.m. | 5/21/2006 | A | Y | Y |
| Jane Givens | 10:30 a.m. | 5/21/2006 | B | Y | N |
| Judy Jones | 11:10 a.m. | 5/21/2006 | A | Y | Y |
| Sandra Collins | 11:20 a.m. | 5/21/2006 | A | Y | Y |

(Column labels: 2800, 2804, 2808, 2812, 2814, 2816)

*Fig. 28*

AUTOMATED APPENDAGE CLEANING APPARATUS WITH BRUSH

CROSS-REFERENCE TO RELATED APPLICATIONS

The present application is a continuation-in-part application of U.S. patent application Ser. No. 11/617,177 filed Dec. 28, 2006, that claimed the benefit of U.S. Provisional Patent Application No. 60/863,753 filed on Oct. 31, 2006. The entire content of the above-referenced applications are incorporated herein by reference in their entireties for all purposes.

FIELD

The present invention relates to automated washing systems, and more particularly, to automated washing systems comprising a novel way of removing debris from hand surfaces and/or fingernails with various brushes, nozzles, and disinfectant solutions.

BACKGROUND

The importance of cleanliness has long been recognized, particularly in the fields of heath-care, food preparation, and laboratories, to name but a few. The practice of surgical scrubbing by surgeons and other operating room personnel is probably the epitome of efforts to cleanse the hands and forearms of persons working in sterile environments. Although manual hand-washing can appear effective, medical experts have concluded that automated hand-washing increases hand-washing compliance and reduces the risk of infection.

Touchless automated hand-washing devices are designed to wash the hands of the user and provide the proper amount of antimicrobial solution in a set time. Additionally, these systems diminish the deterrent effects of friction and irritation associated with frequent manual hand-washing. Notwithstanding the benefits and convenience of automated washing devices, difficulties still exist with removing highly persistent hand contaminants. Accordingly, it would be advantageous to have a system that provides automated washing with a way of providing removal of persistent contaminants on difficult to clean areas of the hands by the intended users.

SUMMARY

In accordance with embodiments of the present invention, various brush, cylinder, and nozzle designs, in conjunction with disinfectant solutions, are disclosed for use in connection with an automated hand-washing station. The system has the capability to ensure that highly soiled areas of the hand can be quickly and effectively cleaned in minimal time within the hand washing system.

In accordance with one or more embodiments described herein, the user utilizes the debris removal hand washing cylinders which have various brushes, high energy spray nozzles, and special disinfecting solutions incorporated in order to obtain extra mechanical interaction with the user's hands in a controlled manner to remove material from the user's hands.

In accordance with embodiments of the present invention, a cleaning station includes one or more cylinders for receiving at least a portion of an appendage of a person. In at least one embodiment, a cleaning station includes a plurality of cylinders that are configured for receiving the person's hands, and may be sized to receive at least a portion of the person's arm, such as a portion of the person's forearm. The cylinders include at least one, and more preferably, a plurality of spray nozzles for delivering water and/or a cleaning fluid or disinfectant to a person's hands. The cleaning stations of the present invention may include non-rotating cylinders, or more preferably, the cylinders rotate during operation, thereby projecting water and/or cleaning fluids around the entire hand during the cleaning cycle.

In accordance with embodiments of the present invention, the cylinders also include one or more friction enhancing structures, such as brushes or pads for contacting at least a portion of the person's appendage, such as the person's hands and/or fingers. In at least one embodiment of the present invention, an end brush is located at a distal end of the cylinder. The end brush is interconnected to the interior distal end of the cylinder. In at least one embodiment of the present invention, a circumferential brush is located around an interior circumference of the cylinder. When the cylinder rotates during a cleaning cycle, the end brush and/or circumferential brush also rotates, thereby allowing the person to position their hand within the cylinder for contacting the end brush.

In accordance with at least one embodiment of the present invention, one more nozzles are located within a brush. It is to be understood that combining a nozzle with a brush is applicable to all of the brushes described herein, including but not limited to end brush and circumferential brush.

The cleaning stations may or may not be operable to record and report data related to user/employee compliance with such requirements.

In use, a person approaches the cleaning station and places a hand in a cylinder. As the cleaning cycle starts, the cylinder begins to rotate and spray water and/or one or more cleaning fluids toward the person's hand. During the cleaning cycle, the person can advance their fingers to contact a brush. As those skilled in the art will appreciate, contacting one's fingers with a brush can assist with removal of debris and/or contaminants to assist with cleaning the person's fingers and hands.

Various embodiments of the present invention are set forth in the attached figures and in the detailed description of the invention as provided herein and as embodied by the claims. It should be understood, however, that this Summary does not contain all of the aspects and embodiments of the present invention, is not meant to be limiting or restrictive in any manner, and that the invention as disclosed herein is and will be understood by those of ordinary skill in the art to encompass obvious improvements and modifications thereto.

Additional advantages of the present invention will become readily apparent from the following discussion, particularly when taken together with the accompanying drawings.

BRIEF DESCRIPTION OF THE DRAWINGS

FIG. 3A is a partial side elevation view with cut-away portions of a cylinder and brush in accordance with embodiments of the present invention;

FIG. 4 is an elevation view down a cylinder having a circumferential brush located therein;

FIG. 5 is an elevation view of a circumferential brush in accordance with an embodiment of the present invention;

FIG. 6 is a side elevation view of a strip of brush prior to bending into a circumferential shape;

FIG. 7 is a plan view of the brush shown in FIG. 6;

FIG. 8 is a perspective view of the brush of FIG. 4 being inserted into a cylinder;

FIG. 9 is a cross-sectional view of a circumferential brush within a cylinder;

FIG. 10 is a partial side elevation view with cut-away portions of a cylinder and brush in accordance with embodiments of the present invention;

FIG. 15 is a side view of a non-rotating cylinder with a rotating brush located in the cylinder, and a user's hand shown interacting with the brush;

FIG. 16A is a partial cut-away perspective view of a cylinder having a circumferential brush located therein, and a user's fingertips shown interacting with the brush;

FIG. 16B is a detail view of a nozzle cooperating with a brush in accordance with an embodiment of the present invention;

FIG. 17 is a partial cut-away perspective view of a cylinder having an end brush located therein, and a user's fingertips shown interacting with the brush;

FIG. 25 is an exemplary cleaning station-use record in accordance with embodiments of the present invention;

FIG. 26 is an exemplary brush replacement record in accordance with embodiments of the present invention;

FIG. 28 is an exemplary compliance report in accordance with embodiments of the present invention.

DETAILED DESCRIPTION

Figure 1:
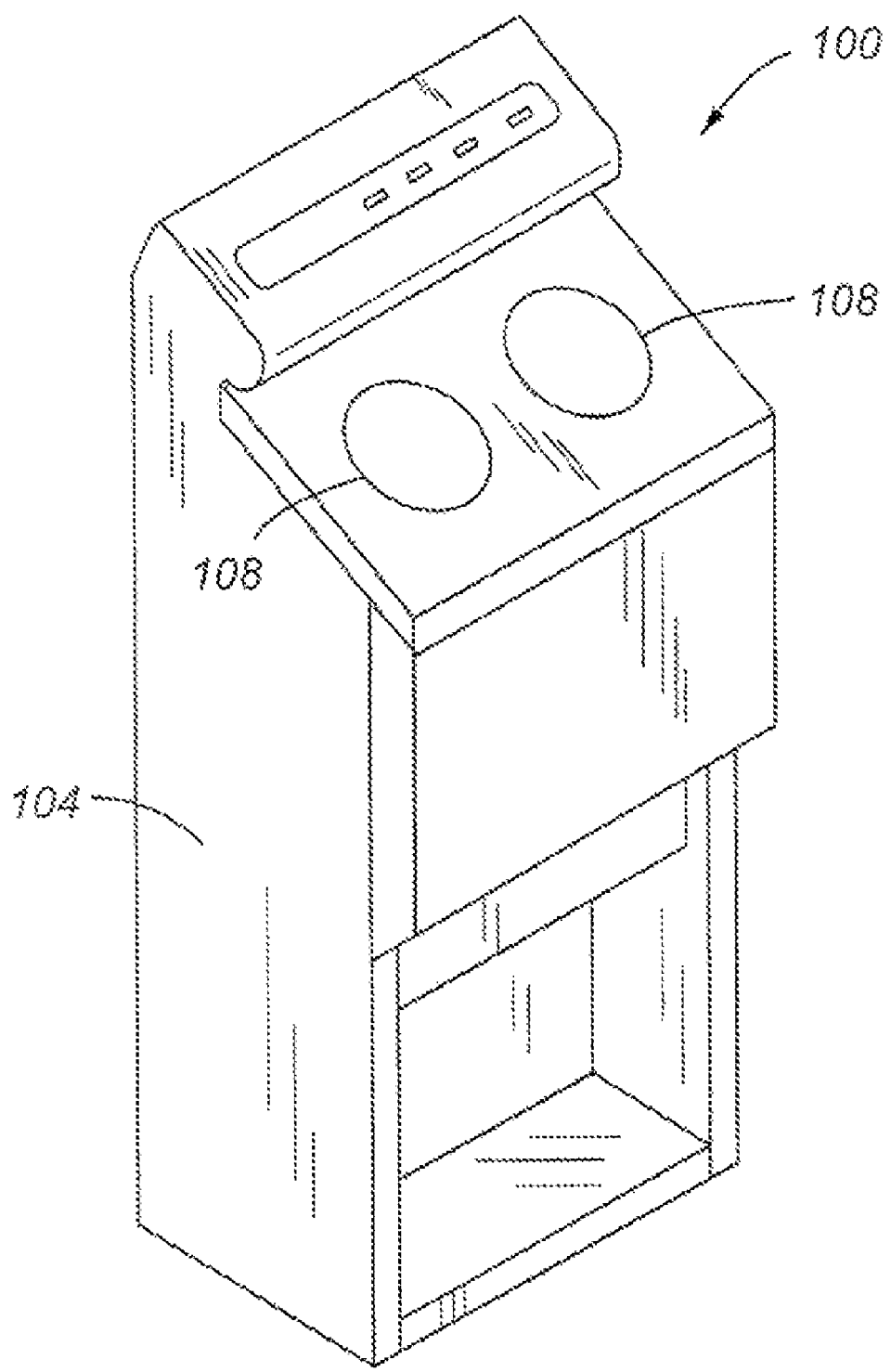
FIG. 1 is a perspective view of a cleaning station in accordance with embodiments of the present invention.

The present invention is directed to a system and method for providing automated washing of an appendage of a person. In addition, it is to be understood that embodiments of the present application are also applicable to other types of washing systems, including for example, boot-washing systems. In accordance with embodiments of the present invention, cleaning effectiveness can be improved from that of traditional sink and faucet systems by using an automated cleaning station with one or more debris removal features. Various embodiments of the present invention are described in the following text and in the drawings; however, it is to be understood that examples described herein are not meant to be limiting. Accordingly, the scope of the present invention includes modifications and alternatives to the example embodiments described in text and shown in the figures associated herewith.

Cleaning stations operate to dispense one or more fluids, such as water, a cleaning fluid, such as soap, and/or a disinfectant, etc., while a person's hands are placed in a washbasin. As used herein, a "washbasin" means a structure associated with the cleaning station where an appendage, such as a hand (or foot/boot) are cleaned, such as one or more wash cylinders, spray areas, pans, tubs, etc. Individuals, such as employees of a laboratory, food service related industry, or health care facility, may be instructed to wash their hands for a minimum amount of time that has been determined to be sufficient to provide a complete cleaning. In situations where hand (or boot) washing is required, or because of personal preferences, the user may be required to use (or otherwise desire to use) an automated cleaning station that incorporates one or more debris removal features.

Embodiments of the present invention include a standard automated cleaning station that is retrofitted with a debris removal feature, such as a brush, or a cylinder that accepts one or more different types of brushes. In addition, embodiments of the present invention include automated cleaning stations that if the user requires further debris removal than the standard station allows for, they may use a "debris removal station" or a unit that allows for both the regular washing and debris removal within the same unit.

Referring now to FIG. 1, an automatic cleaning station 100 is depicted. The cleaning station 100 includes a body 104 and a pair of washbasins, and more preferably, cylinders 108 residing within the body 104 for receiving an appendage of the user. Embodiments of the present invention include at least one washbasin that comprises a cylinder 108 that rotates around a user's hand to clean the user's hand. Cleaning is performed by the application of fluids to the hands, wherein the fluids include water, a cleaning agent (such as soap), and/or a disinfectant, such as chlorhexidine gluconate (CHG). The fluids are directed toward the user's hands through a series of nozzles, wherein the nozzles provide coverage of cleaning fluids to the user's hand to clean and rinse the user's hand.

Figure 2:
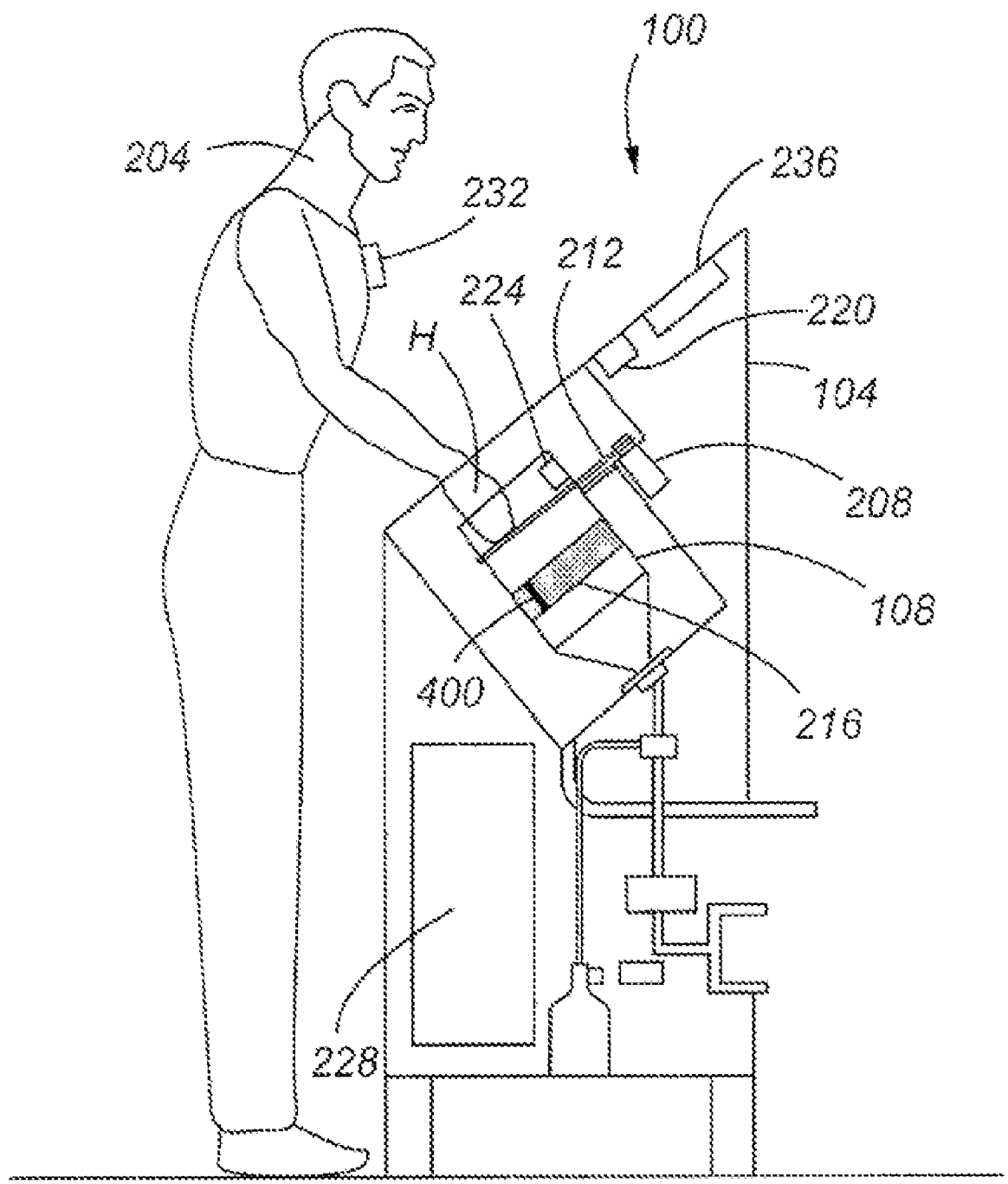
FIG. 2 is a schematic depiction of a user at a cleaning station.

Referring now to FIG. 2, a user 204 is shown adjacent a cleaning station 100. The user 204 may be an employee or visitor of a facility who is required to wash their hands because of the nature of their work or the nature of the facility. The user 204 is advancing his hand H into the cylinder 108. The cleaning station 100 shown in FIG. 2 includes a motor 208 and associated tubing 212 to rotate the cylinder 108 around the hand H of user 204. Nozzles (not shown) direct fluids toward the hand H of the user 204. In accordance with a first embodiment of the present invention, the cylinder 108 also comprises a circumferential brush 216. The circumferential brush 216 resides within the interior area of the cylinder 108 and allows for mechanical interaction between the hand H of the user 204 the circumferential bush 216 within the cleaning environment of the cylinder 108 to augment the cleaning process. Alternative to a brush type structure, and for all structures identified as a "brush" or "brushes" herein, the mechanical interaction may be applied by any suitable type of friction enhancing structure, wherein such friction enhancing structure includes, but is not limited to, a brush, pad, sponge, non-fluid tactilely perceptible material, and combinations thereof.

Referring now to FIG. 3A, an enlarged view of a cylinder 108 with a circumferential brush 216 is shown. The circumferential brush 216 includes a backing 304 and bristles 308. FIG. 3A illustrates a two-part partial cut-away view of cylinder 108 wherein a portion of the cylinder 108 in the vicinity of the circumferential brush 216 is omitted. More particularly, the upper portion 310 (relative to the sheet of paper) of the cylinder 108 at the circumferential brush 216 in FIG. 3A illustrates a cut-away of only the cylinder 108 in the vicinity of the circumferential brush 216, and the lower part 311 (relative to the sheet of paper) of the cylinder 108 at the circumferential brush 216 illustrates a cut-away of the cylinder 108 and the backing 304 to show the bristles 308. The bristles 308 of the circumferential brush 216 extend toward the longitudinal and rotational axis A-A of the cylinder 108. As those skilled in the art will appreciate, an end of the bristles 308 is set within or otherwise secured to the backing 304. As best seen in FIG. 4, the backing 304 includes a radial outer surface 404. Referring to FIG. 5, in one embodiment of the invention the radial outer surface 404 of the circumferential brush 216 contacts or is interconnected to an inner surface 504 of the cylinder 108. The circumferential brush 216 thus forms a rotating brush within the cylinder 108 for allowing the user to contact a skin surface with the circumferential brush 216 to provide mechanical friction to the skin surface during the cleaning process.

The circumferential brush 216 may be detachably attached to the cylinder using a variety of ways. For example, an adhesive may be used. More preferably, a frictional interconnecting mechanism is employed to hold the circumferential brush 216 within the cylinder. For example, the backing 304 of the circumferential brush 216 may include suction cups and/or other textural features for cooperating with the inner surface 504 of the cylinder 108.

Figure 3B:
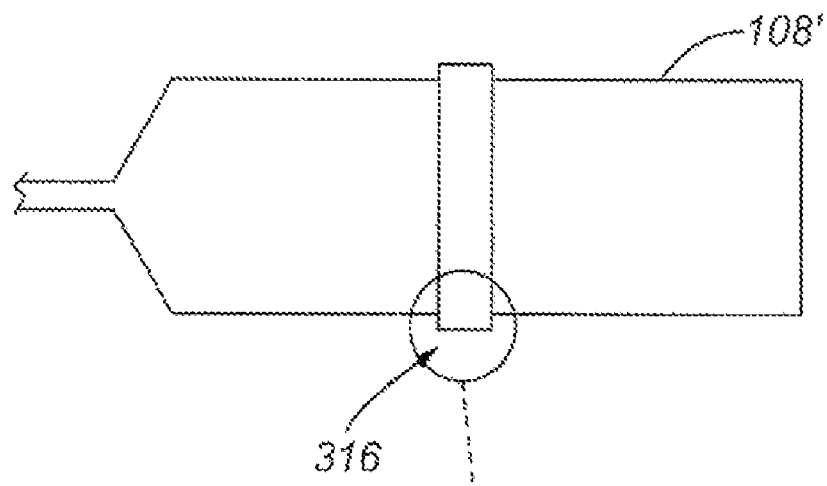
FIG. 3B is a side elevation view of a cylinder having a channel for a circumferential brush.
Figure 3C:
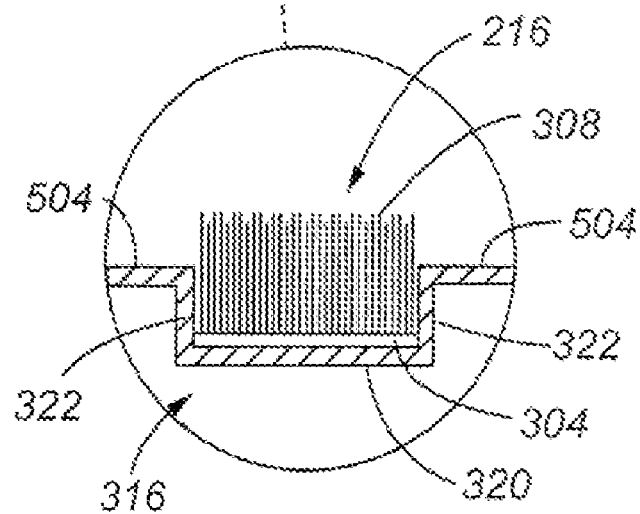
FIG. 3C is a detailed cross-sectional view of the channel shown in FIG. 3B.

Referring now to FIGS. 3B-3C, a modification of the cylinder is shown wherein the cylinder includes one or more supplemental structural features for accommodating circumferential brush 216. As one example, cylinder 108' of FIG. 3B includes a channel 316 for receiving the circumferential brush 216. In accordance with at least one embodiment of the invention, the channel 316 includes a recessed wall 320, where the recessed wall 320 has a width that is sized to accommodate the circumferential brush 216. More particularly, and referring now to the detail drawing of FIG. 3C, the recessed wall 320 receives the backing 304 of the circumferential brush 216, thereby positioning the backing 304 in a recessed location relative to the adjacent inner surface 504 of the cylinder 108'. In accordance with embodiments of the present invention, the channel 316 may include retention features for assisting with detachably securing the circumferential brush 216. For example, the recessed wall may include structure for frictionally engaging the circumferential brush 216. Alternatively, the separation distance between the lateral walls 322 are sized for providing a lateral holding force against the circumferential brush 216. In yet another alternative, the recessed wall 320 and brush may use magnetic components for assisting the securing the circumferential brush 216 within the channel 316.

Figure 3D:
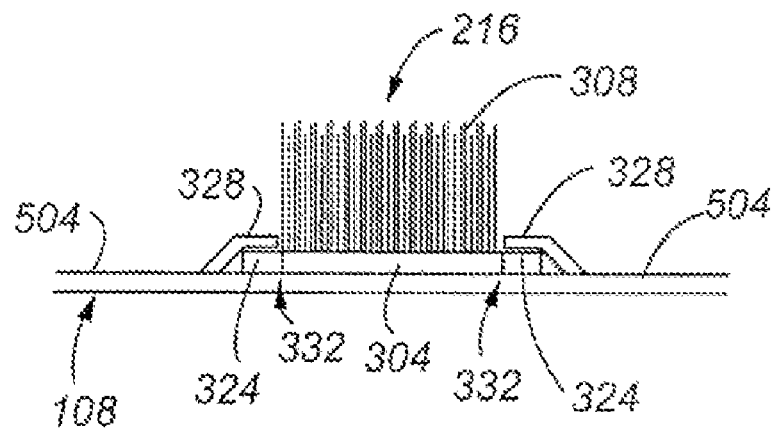
FIG. 3D is a detailed cross-sectional view of another embodiment of a mechanism for holding a circumferential brush.

Referring now to FIG. 3D, a detail drawing of a different way of holding a circumferential brush 216 is shown. Circumferential brush 216 of FIG. 3D includes a blank portion or unbristled area 324 for engaging backing receiver 328. The backing receiver 328 preferably is configured for frictionally engaging the unbristled area 324 of the backing 304, thereby holding the circumferential brush 216 in place. The circumferential brush 216 is positioned within the backing receiver 328 by slipping the blank portion or unbristled area 324 under the backing receiver 328 along the lateral edges 332 of the circumferential brush 216.

As those skilled in the art will appreciate, one issue associated with a cleaning station is the actual cleanliness of the cleaning station itself. More particularly, for cleaning stations employing a brush, the sanitation of the brush should be maintained. In accordance with embodiments of the present invention, a variety of ways of maintaining a sanitary brush are employed. In accordance with at least one embodiment of the invention the brush or brushes can be removed from the cleaning station for disinfecting, such as by application of a disinfectant to the brush after the brush is removed from the cleaning station. Alternatively, the brush can be disinfected within the cleaning station by applying a disinfectant to the brush. In accordance with at least one embodiment of the invention the brush is considered disposable and is replaced after a specified period of time, for example, after each day of use. Embodiments of the present invention incorporate quick-change features for allowing the brushes to be replaced. Such quick-change features include, but are not limited to, the channel 316 and backing receivers 328 already described above and shown in FIGS. 3C and 3D. In accordance with at least one embodiment of the invention the brush itself includes one or more anti-microbial materials for promoting and maintaining sanitary conditions within the environment of the cylinders, and in particular, within the environment of the brush itself. The anti-microbial materials may include surface applications of anti-microbial materials to the brush, as well as anti-microbial materials that are impregnated in or formed as part of the brush components, including its bristles. The following U.S. patents are incorporated herein by reference in their entirety: U.S. Pat. Nos. 5,238,749; 5,340,581; 5,503,840; 6,235,351; 6,413,921; and 6,902,397.

Cylinders that are too large result in excess use of cleaning fluids and water, as well as extended flush periods to transition between cleaning stages, such as when transitioning between a cleaning fluid wash stage and a rinse stage using water. Cylinders that are too small do not necessarily allow for the user's hand to comfortably fit in the cylinder. In accordance with at least one embodiment of the invention, the cylinder 108 for a hand washing type cleaning station 100 has a diameter D of between about 3 to 10 inches, and more preferably, the cylinder 108 has a diameter D of between about 4 to 7 inches, and more preferably yet, the cylinder 108 has a diameter D of between about 5 to 6 inches, and still more preferably yet, the cylinder 108 has a diameter D of about 5.25 inches. Such dimensions are appropriate for a hand-washing-type cleaning station for adults. However, as those skilled in the art will appreciate, smaller diameter cylinders may be appropriate for a handwashing-type cleaning station for use, for example, in a children's school. Likewise, larger diameter cylinders maybe appropriate for cleaning a person's leg.

As best seen in FIG. 6, the circumferential brush 216 may be formed in a strip and subsequently curved to form its circular shape and installed in the cylinder 108, or the circumferential brush 216 may be provided in a circular shape ready for insertion into the cylinder. Utilizing a brush of limited surface area provides an advantage because of a limited replacement cost such that regular installation of a new brush is economically feasible. As best seen in FIGS. 7 and 8, a circumferential brush 216 preferably has a width W of about 0.5 to 6 inches, and more preferably, has a width W of about 0.75 to 4 inches, and more preferably yet, has a width W of about 1 to 2 inches. Thus, in accordance with embodiments of the present invention, the surface area of a circumferential brush 216 preferably is between about 4 and 200 in$^2$, and more preferably, the surface area of the circumferential brush 216 is between about 10 and 100 in$^2$, and more preferably yet, the surface area of a circumferential brush 216 is between about 15 and 40 in$^2$, and still more preferably yet, the surface area of a circumferential brush 216 is about 25 in$^2$.

Referring now to FIG. 8, circumferential brush 216 is being inserted into cylinder 108. FIG. 9 illustrates a cross-sectional view of cylinder 108 with circumferential brush 216 located within the cylinder 108. In accordance with at least one embodiment of the invention, the circumferential brush 216 is preferably located distally of a longitudinal midpoint M of cylinder 108. Accordingly, the circumferential brush 216 resides within the lower distal half of the cylinder 108. Such brush location allows the nozzles of the cylinder to cooperate with the user's hand and circumferential brush 216 to improve removal particulates, debris, and/or substances from the user's hand.

Figure 11:
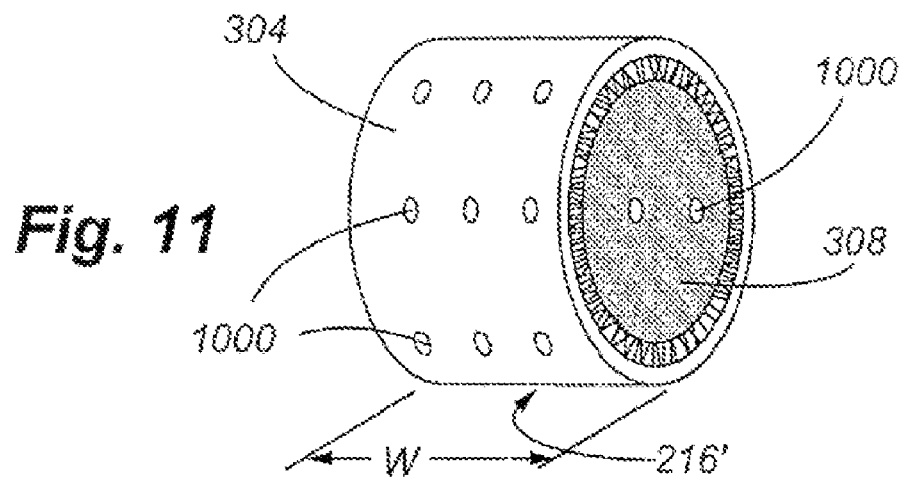
FIG. 11 is a perspective view of the brush shown in FIG. 10.

Referring now to FIG. 10, and in accordance with at least one embodiment of the invention, circumferential brush 216' is shown within a non-rotatable cylinder 108. FIG. 11 illustrates a perspective view of the circumferential brush 216'. The circumferential brush 216' includes at least one orifice 1000, and more preferably, a plurality of orifices 1000 that allow cleaning fluids and/or disinfectants, including brush disinfectants, to be transmitted through the circumferential brush 216' itself. More particularly, and with reference to FIGS. 10 and 11, a circumferential brush 216' is shown having a width W substantially equal to or greater than the diameter D of the cylinder 108, wherein the circumferential brush 216' includes orifices 1000 for conveying fluid through the circumferential brush 216' and into the interior space of the cylinder 108. In at least one embodiment, the brush surfaces are installed throughout the inner surface of the cylinder. In addition, such brush surfaces are installed in front of flow-through disinfectant nozzles that push any debris out of the brushes during usage and at the same time disinfect the brush material. In accordance with at least one embodiment of the present invention, a debris removal cylinder is provided that comprises a permanent brush lining, wherein the cylinder includes the orifices 1000 serving as cleaning fluid projection nozzles and also as flow-through disinfectant nozzles that will constantly clean the brush.

FIG. 10 is illustrates a two-part partial cut-away view of cylinder 108 wherein a portion of the cylinder 108 in the vicinity of the circumferential brush 216' is omitted. More particularly, the upper portion 1010 (relative to the sheet of paper) of the cylinder 108 at the circumferential brush 216' in FIG. 10 illustrates a cut-away of only the cylinder 108 in the vicinity of the circumferential brush 216', and the lower part 1011 (relative to the sheet of paper) of the cylinder 108 at the circumferential brush 216' illustrates a cut-away of the cylinder 108 and the backing 304 to show the bristles 308.

Figures 12, 13, 14:
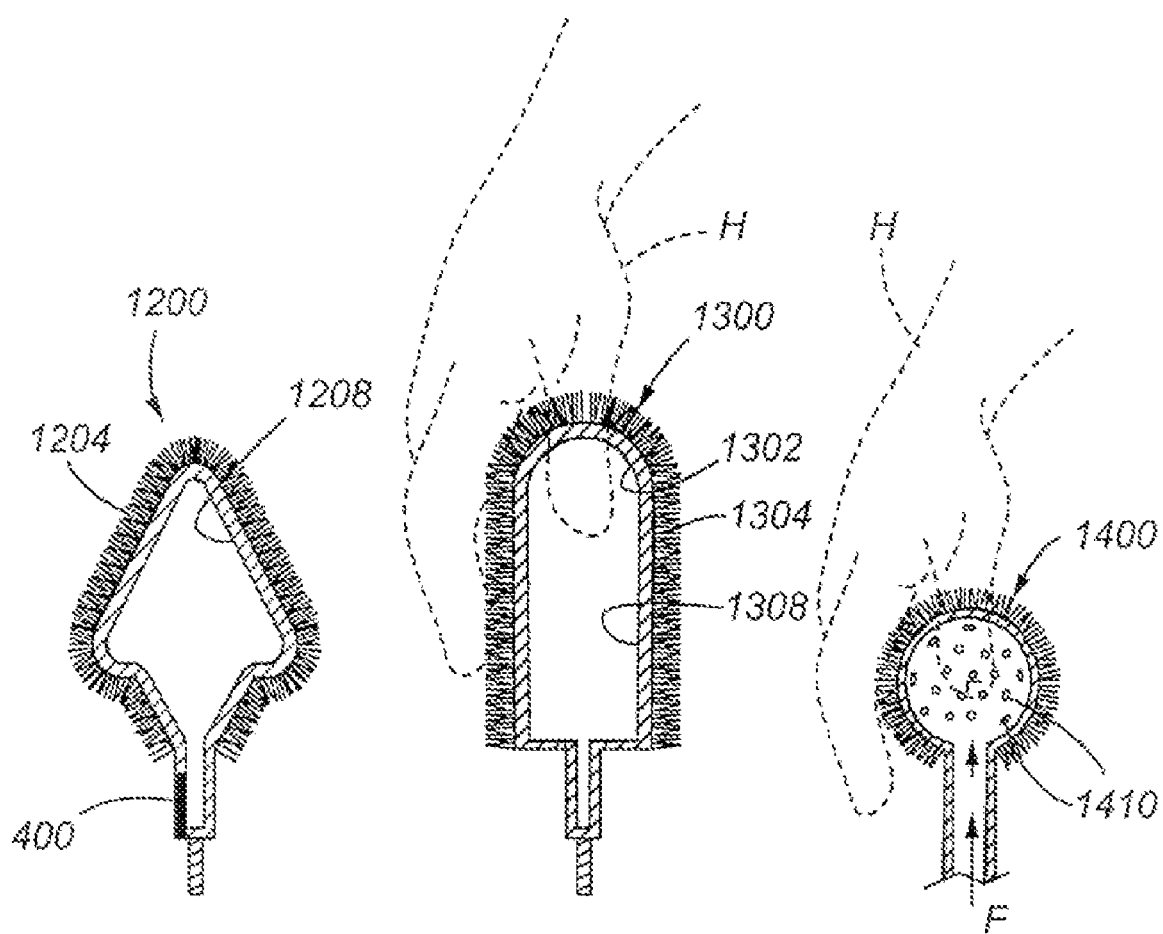
FIGS. 12-14 are cross-section views of several end brushes in accordance with embodiments of the present invention.

Referring now to FIGS. 12-14, and in accordance with embodiments of the present invention, a series of various end brushes are illustrated for use with cleaning station 100. The end brushes may be used in a cylinder having a circumferential brush 216, 216' described above. The end brushes are generally configured to include a distal end for facilitating interconnection to the interior distal end of the cylinder 108, such as by a threaded connection. The threaded connection or structure adjacent the threaded connection may include a sealing device such as an o-ring for preventing or limiting water and/or cleaning fluids from passing through the interconnection opening.

Referring now to FIG. 12, a conical-shaped brush 1200 is shown. Conical-shaped brush 1200 is configured for placement within the distal end of the cylinder 108. Conical-shaped brush 1200 features bristles 1204 that are located on the exterior of the conical body 1208. The conical-shaped brush 1200 is suited for allowing a user to contact his or her fingers, fingertips, finger nails, and/or palms with bristles 1204.

Referring now to FIG. 13, a cylindrical-shaped brush 1300 is shown, wherein the cylindrical-shaped brush 1300 is also configured for placement within the distal end of the cylinder 108. The cylindrical-shaped brush 1300 includes a semi-spherical portion 1302 at is first end, and a way (e.g., a threaded post, reverse threaded post, etc.) of interconnecting the brush to the cylinder 108 at its second end. Cylindrical-shaped brush 1300 also features bristles 1304 that are located on the exterior of the cylindrical body 1308. The cylindrical-shaped brush 1300 is suited for allowing a user to contact his or her fingers, fingertips, finger nails, and/or palms with bristles 1304.

Referring now to FIG. 14, a spherical-shaped brush 1400 is shown, wherein the spherical-shaped brush 1400 is also configured for placement within the distal end of the cylinder 108. The spherical-shaped brush 1400 includes features similar as those described above for the conical-shaped brush 1200 and the cylindrical-shaped brush 1300. In addition, the spherical-shaped brush 1400 includes openings 1410, where the openings 1410 may comprise orifices or nozzles for projecting a flow F of cleaning fluid to the hand H of the user 204 during a cleaning cycle, and/or for releasing disinfectant to sanitize the brush itself. Although not shown, the conical-shaped brush 1200 and the cylindrical-shaped brush 1300 may also include openings 1410, where the openings 1410 may comprise orifices or nozzles for projecting a flow F of cleaning fluid to the hand H of the user 204 during a cleaning cycle, and/or for releasing disinfectant to sanitize the brush itself. In accordance with at least one embodiment of the present invention, FIG. 15 is a depiction of a cylinder with a spherical-shaped brush 1400 attached to the bottom of the cylinder 1500, wherein the brush 1400 includes flow-through disinfectant nozzles or openings 1410 that will constantly clean the brush. As shown in FIG. 15, the spherical-shaped brush 1400 may rotate, as shown by rotational arrow R within non-rotating cylinder 1500.

FIGS. 15, 16A and 17 depict how various versions of how a debris removal cylinder may be used to clean the fingers and fingertips with the components that may be included in embodiments of the present invention. In use, the user inserts their hand H into the cylinder 108 and the cleaning station 100 automatically initiates a cleaning cycle by reading the presence of the user's hand H within the cylinder 104, such as by an optical sensor 224 shown in FIG. 2. As shown in FIG. 16A, the user may advance their hand H in the cylinder to contact a friction enhancing structure, such as circumferential brush 216. FIG. 16A is a depiction of a cylinder with a removable brush strip or circumferential brush 216 having flow through disinfectant nozzles that will constantly clean the brush in accordance with embodiments of the present invention. Thus, the circumferential brush 216 may include one or more openings or nozzles 1600 for projecting cleaning fluid to the hand H of the user 204 during a cleaning cycle, and/or for releasing disinfectant to sanitize the brush itself. The nozzles may project through the backing 304 and include structure for engaging the backing 304 to secure the circumferential brush 216 in place against the inner surface 504 of the cylinder 108. Referring now to FIG. 16B, and in accordance with an embodiment of the present invention, the nozzle 1600 may extend interior of the inner surface 504 of the cylinder 108. In addition, the nozzle 1600 may include a flange 1604 for engaging the circumferential brush 216. As shown in FIG. 16B, the flange 1604 engages a blank portion or unbristled area 336 of the circumferential brush 216 that is situated concentric to the nozzle 1600. Therefore, the nozzle 1600 provides duel functionality by serving to project fluids such as water, soap, and/or disinfectants, while also serving to retain the circumferential brush 216 in its proper position.

Referring now to FIG. 17, rotating cylinder 108 is shown with conical-shaped brush 1200. As shown in FIG. 17, the user may advance their hand H to contact the conical-shaped brush 1200. Nozzles 1700 dispense cleaning fluids to the hand during the cleaning cycle.

Figure 18:
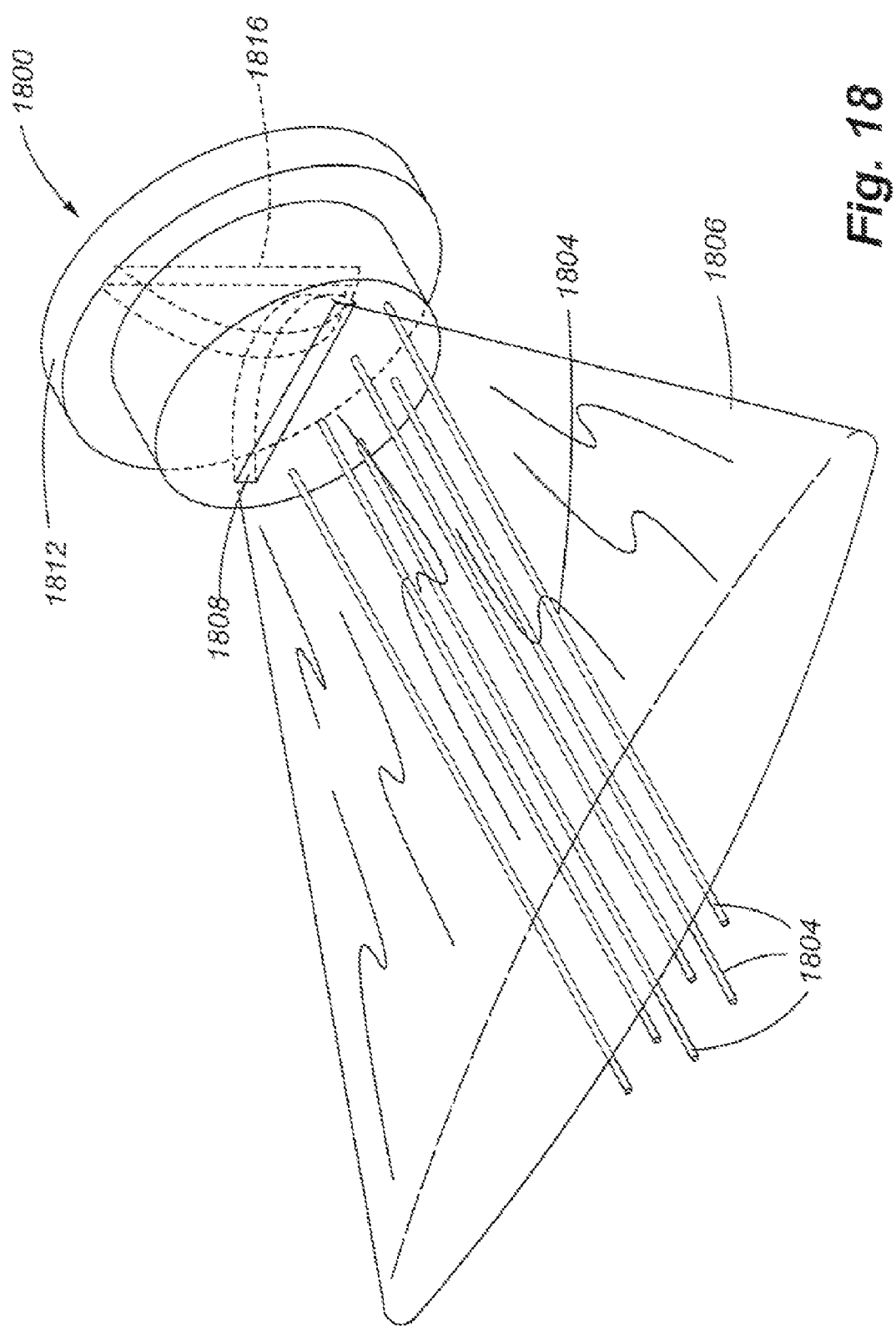
FIG. 18 is a perspective view of a nozzle having a brush component.

Referring now to FIG. 18, a brush nozzle 1800 is shown, wherein the brush nozzle 1800 includes at least one, and more preferably, a plurality of co-located bristles 1804. More particularly, the brush nozzle 1800 comprises a nozzle outlet 1808 for dispensing one or more of water, soap, and disinfectant. In addition, bristles 1804 are connected directly to the nozzle housing 1812. The bristles 1804 are preferably about 1 to 3 inches in length, and have a diameter of between about 0.0.20 to 0.040 inch. The nozzle housing 1812 is about 0.5 to 1.0 inch in diameter and includes the nozzle outlet 1808 for projecting a substantially flat fan spray 1806 of fluid. The bristles 1804 are positioned to intercept the flat fan spray 1806. For the brush nozzle 1800, water enters an entry aperture 1816 and exits the nozzle 1800 at nozzle outlet 1808. When used in combination with a rotating cylinder, the fan spray 1806 wets the bristles 1804, and the bristles 1804 and fan spray 1806 rotate and contact the user's skin to remove particulates, substances and/or biological matter. The nozzle 1800 with co-located bristles 1804 may be used with one or more of the circumferential brushes or end brushes described herein.

Figure 19:
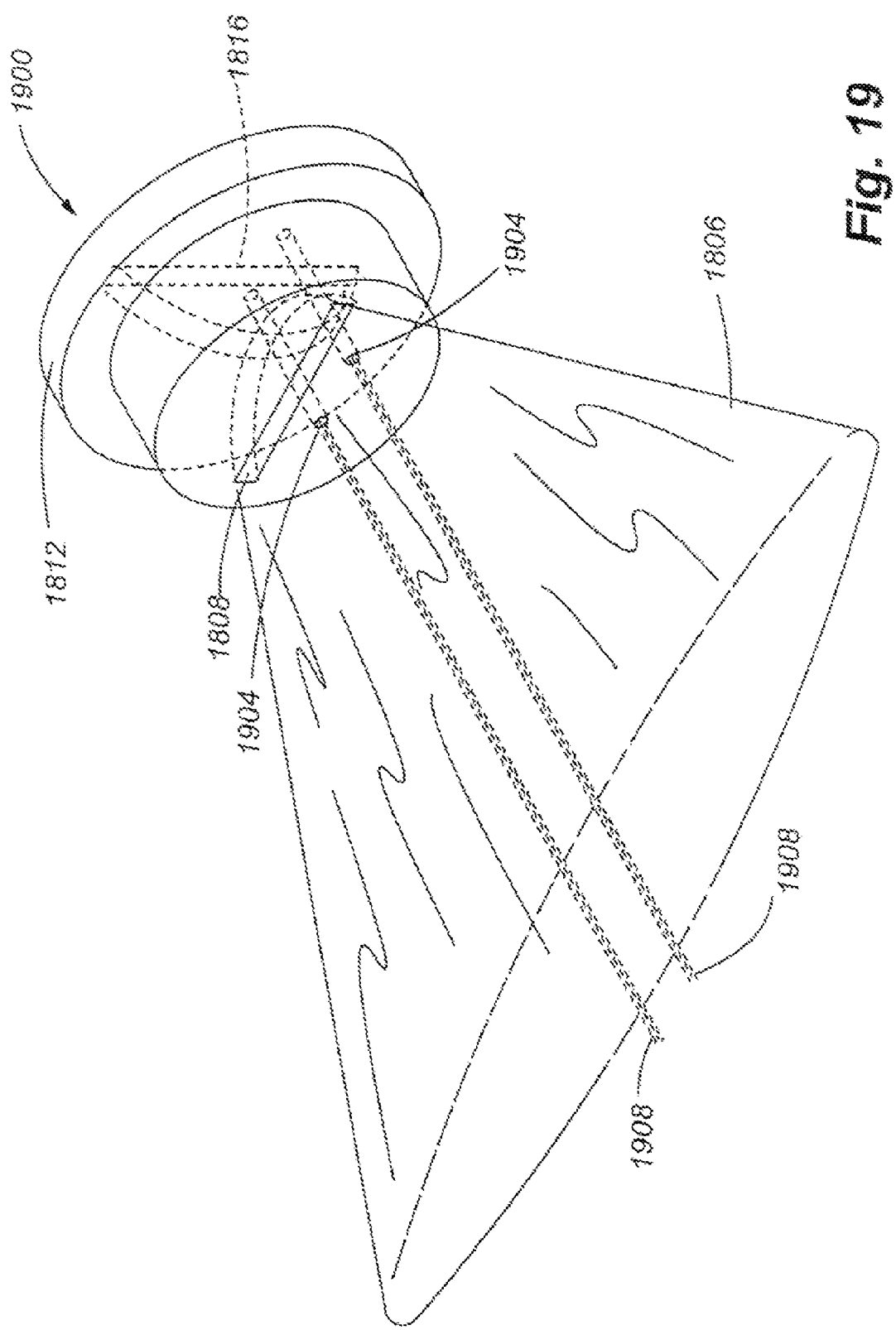
FIG. 19 is a perspective view of a dual action nozzle.

Referring now to FIG. 19, a dual flow nozzle 1900 is shown, wherein the dual flow nozzle 1900 is configured for use with a cleaning station 100, and is applicable for use with both rotating and non-rotating cylinders. The dual flow nozzle 1900 includes a nozzle housing 1812 that is about 0.5 to 1.0 inch in diameter and includes nozzle outlet 1808 for projecting a substantially flat fan spray 1806 of fluid. In addition, the dual flow nozzle 1900 includes at least one supplemental aperture 1904 for projecting a focused debris removal stream 1908 of flow toward the hand of the user. The focused debris removal stream 1908 preferably comprises a stream of fluid having a diameter of between about 0.020 and 0.080 inch. For the dual flow nozzle 1900 shown in FIG. 19, the nozzle 1900 includes two supplemental apertures 1904 for projecting two focused debris removal streams 1908. The dual flow nozzle 1900 may be used with cylinders 108 having one or more of the circumferential brushes and/or end brushes described herein. In use, the flat fan spray 1806 also aids in controlling fluid splashing out from the cylinder 108 where the splashing fluid is generated from the focused debris removal stream(s) contacting the user's skin.

Figures 20, 21:
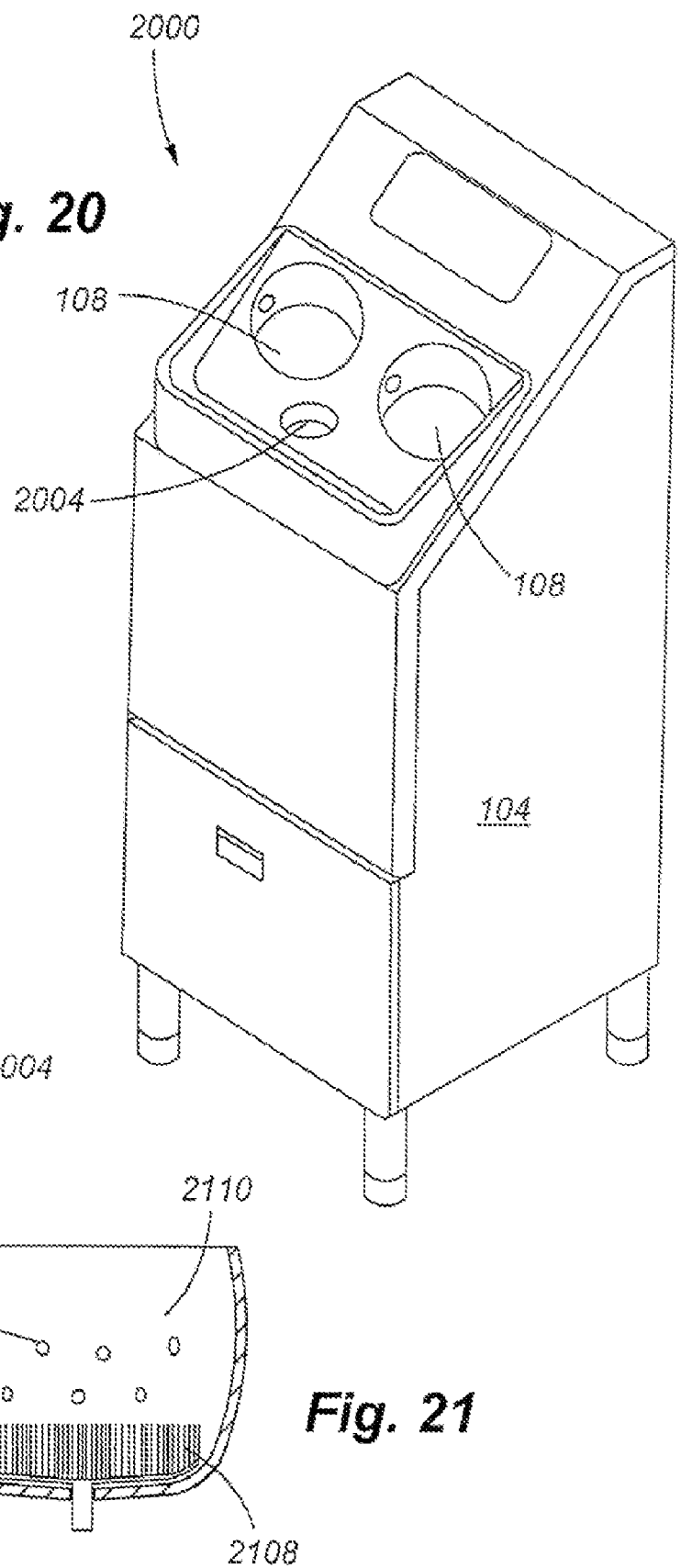
FIG. 20 is a perspective view of a cleaning station having a third dedicated debris removal cylinder for a user's fingertips.
FIG. 21 is a cross-sectional view of the debris removal cylinder shown in FIG. 20.
Figure 22:
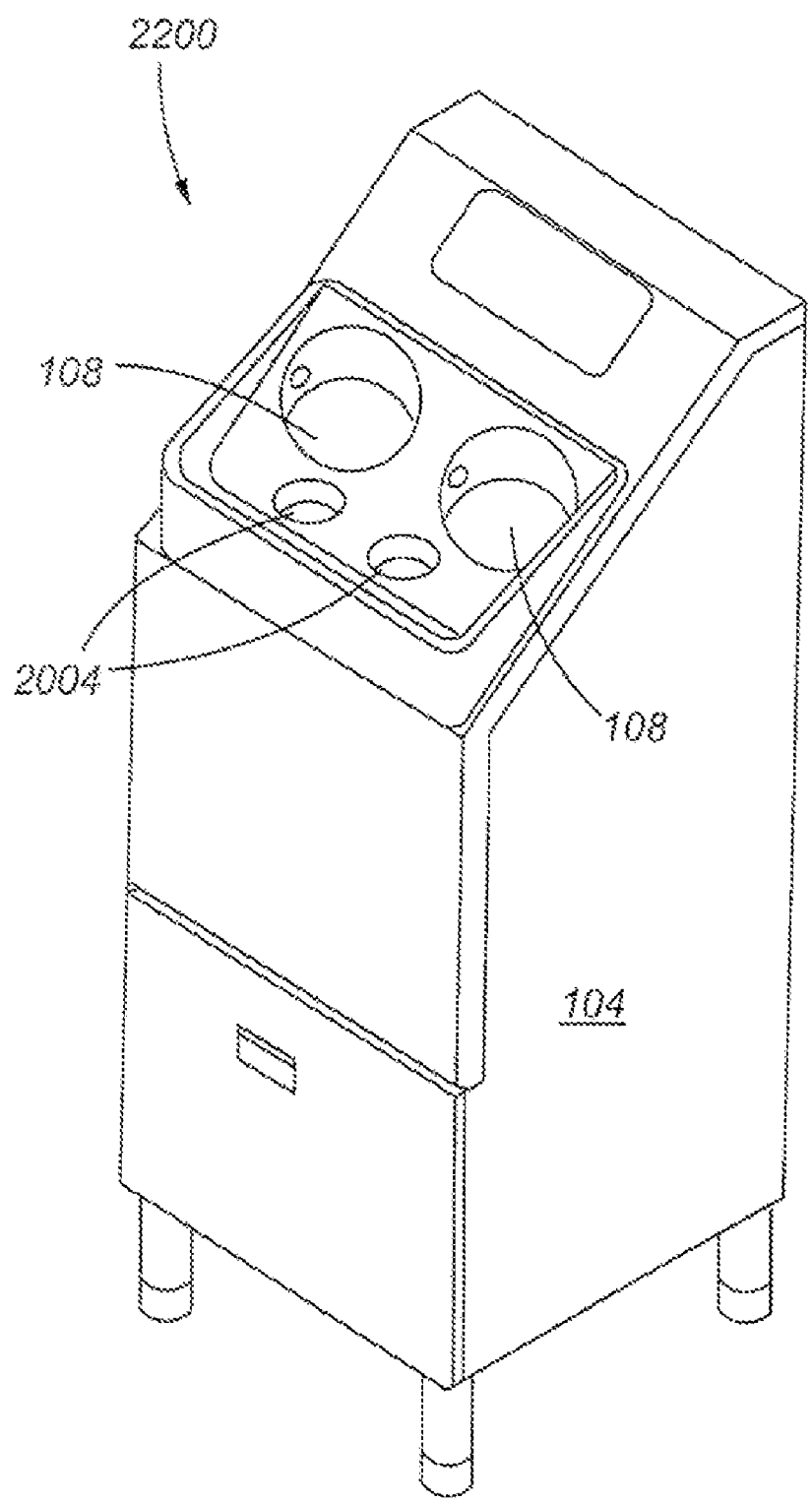
FIG. 22 is a perspective view of a cleaning station having third and fourth dedicated debris removal cylinders for a user's fingertips.

Referring now to FIG. 20, a modified cleaning station for the removal of debris is shown in the form of cleaning station 2000. Cleaning station 2000 includes two cylinders 108 as described above, and also includes a third cylinder in the form of fingertip cleaning cylinder 2004. As shown in FIG. 21, fingertip cleaning cylinder 2004 preferably comprises a cylinder with a brush element located at its distal end for cleaning the fingertips of the user. The fingertip cleaning cylinder 2004 preferably rotates and spins circular end brush 2108. Circular end brush 2108 is preferably detachably attached using a quick change fitting, such as a threaded coupling or other mechanism, and may include disinfecting nozzles of its own as described above. In accordance with at least one embodiment, a plurality of nozzles 2112 within the cylinder wall 2110 direct fluids toward the fingers and fingertips of the user. Referring now to FIG. 22, a cleaning station 2200 is shown having a pair of fingertip cleaning cylinders 2004. Thus, a cleaning station may include one or more dedicated debris removal cylinders, and/or it may comprise cylinders with friction enhancing structures such as brushes for removal of particulates, substances and biological matter.

In accordance with at least one embodiment of the invention, an RFID tag may be incorporated into a brush of the present invention for monitoring installation of a new brush on a prescribed basis, and ensuring that old brushes are not reused. Referring again to FIG. 4, a brush RFID tag 400 is shown within the backing 304 of brush 216. It is to be understood that utilization of an RFID tag with all brushes and/or friction enhancing structures described herein is encompassed by the scope of the present invention, whether the brush or friction enhancing structure is a circumferential brush 216 or other brush, such as distally located end brushes described below, or a pad, sponge, or other tactilely perceptible device, as well as combinations thereof.

Referring again to FIG. 2, and in accordance with one or more embodiments of the present invention, the cleaning station 100 includes an RFID reader 220. The RFID reader 220 is positioned so as to be able to read the brush RFID tag 400 when the brush is positioned within the cleaning station 100. The RFID reader 220 may be incorporated into the cleaning station 100 or, alternatively, may be implemented as a stand-alone device. For example, the RFID reader 220 may be positioned adjacent to the cylinders 108 associated with the cleaning station 100. The cleaning station 100 may also include an optical sensor 224 positioned so as to be able to sense a hand H of the user 204 when the user's hand is placed within the cylinder 108 in a position where they will properly receive cleaning fluids, such as water, soap and/or disinfectant as dispensed by the cleaning station 100. The RFID reader 220 is preferably in communication with a cleaning station operations monitor 228, which, in turn, is operable to collect data associated with the cleaning station 100, including the brush RFID tag 400. In at least one embodiment of the invention, the user 204 may also wear an RFID tag 232 to provide identification of the user 204. In particular, data is collected from the RFID reader 220 indicating the identity of the user 204. Additionally, the cleaning station operations monitor 228 records the length of time in which the hands of the user 204 were placed in the cylinder 108 as indicated by the optical sensor 224. In addition and/or alternative to RFID, other methods of brush identification are within the scope of the present invention. In particular, the brush may be identified by typing in a brush unit member in a key pad or other data entry device, or by scanning a bar code associated with the brush, etc.

Figure 23:
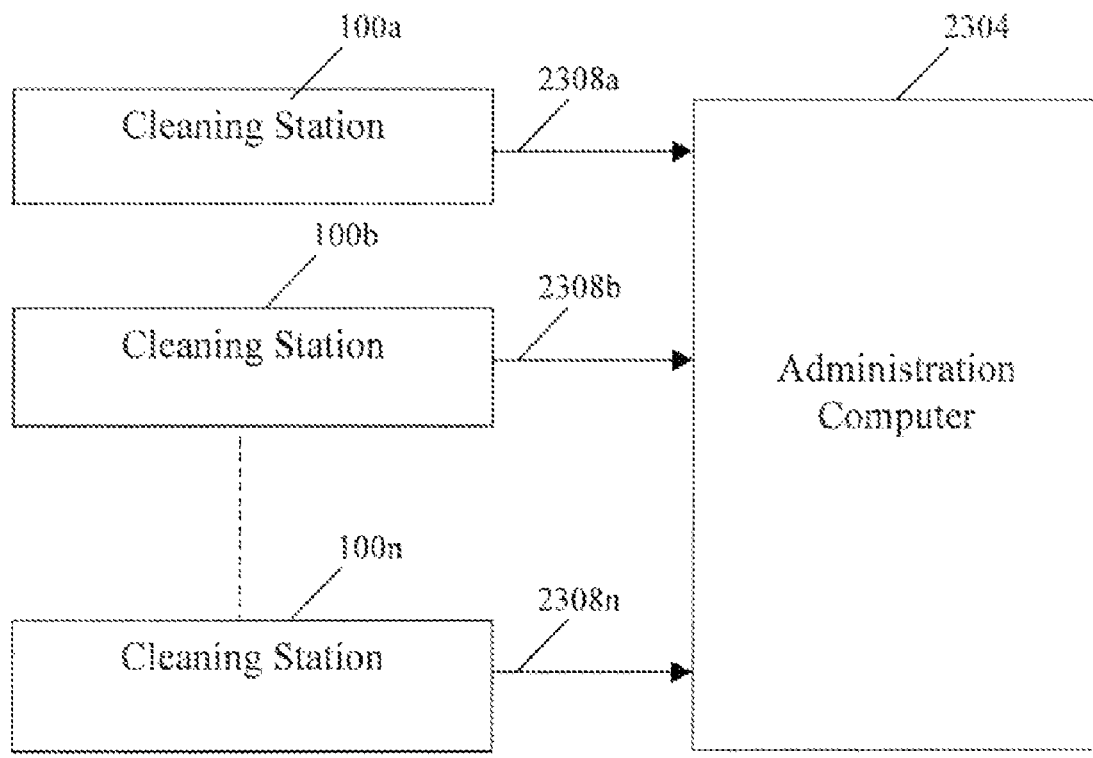
FIG. 23 is a block diagram of components that may be included in verification related embodiments of the present invention.

Referring now to FIG. 23, components of a compliance system for demonstrating, among other things, brush sanitation and maintenance in accordance with embodiments of the present invention are illustrated in block diagram form. Shown in FIG. 23 is a plurality of cleaning stations 100a, 100b . . . 100n. The cleaning stations 100a-100n may be used by people employed at a facility that requires employees to wash their hands. Such facilities may include, for example, restaurants, food processing facilities, hospitals and laboratories. Also shown in FIG. 23 is an administration computer 2304 for use by a manager or administrator of the facility. The administration computer 2304 is operable to generate a compliance report as described herein.

The administration computer 2304 communicates with the cleaning stations 100a-100n over a plurality of communication links 2308a, 2308b . . . 2308n. The communication links may be implemented by any one of a variety of methods and may depend on the type of facility in which the cleaning stations 100a-100n are used. In particular, the communication links 2308a-2308n may be implemented as part of a local area network (LAN) or a wide area network (WAN). More particularly, the communication links 2308a-2308n may be implemented using such protocols as Ethernet or USB. The communications links 2308a-2308n may be implemented as wired or wireless connections. It may be the case that the administration computer 2304 is located in a separate facility from one or more of the cleaning stations 100a-100n. In this case, a distributed data network such as the Internet may form part of the communication links 2308a-2308n.

Figure 24:
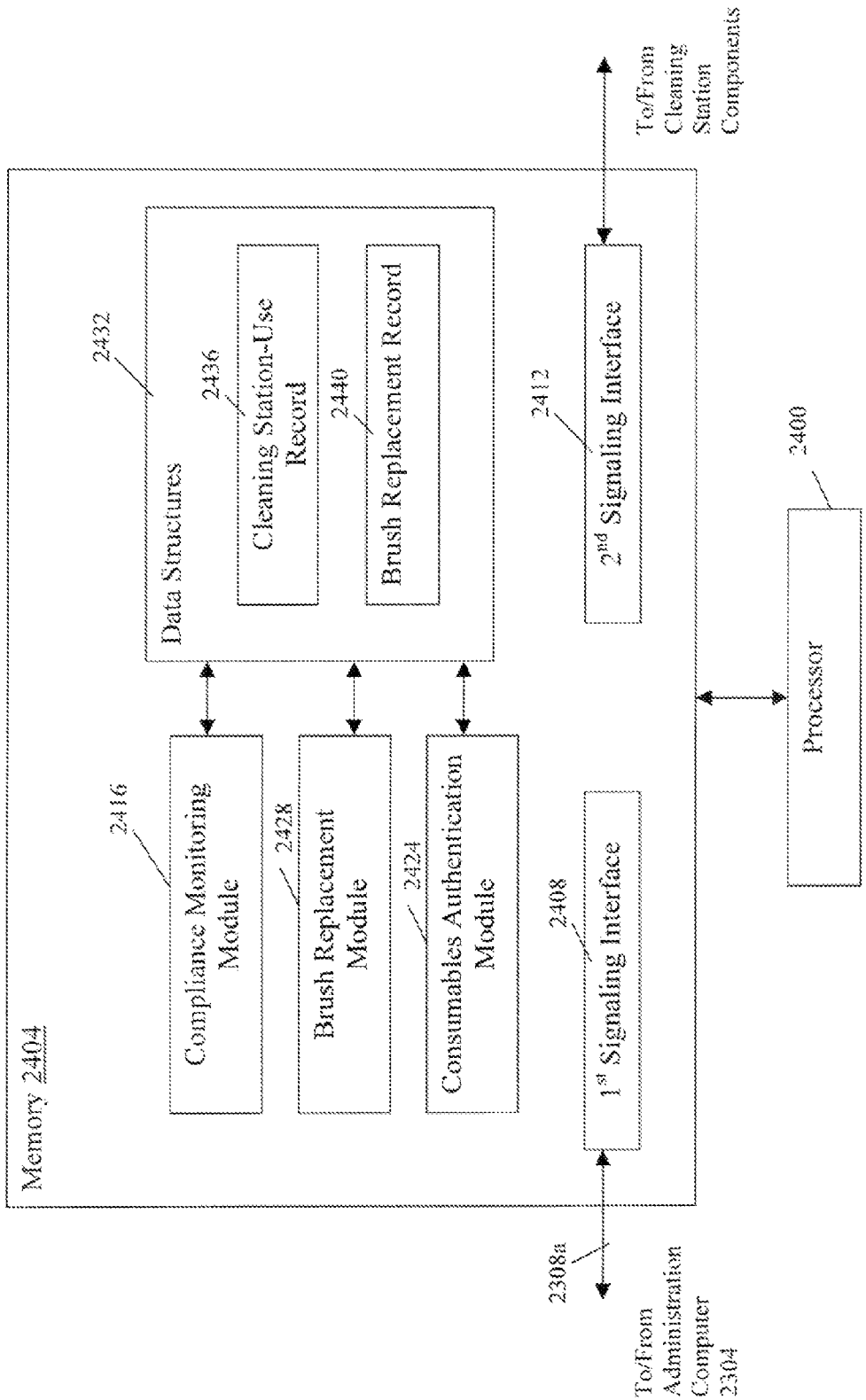
FIG. 24 is a block diagram of a cleaning station operations monitor in accordance with embodiments of the present invention.

Referring now to FIG. 24, a block diagram of components and features of the cleaning station operations monitor 228 is shown. The cleaning station operations monitor 228 is a computational device. Accordingly, the cleaning station operations monitor 228 includes a processor 2400, a memory 2404 and signaling interfaces 2408 and 2412 operable to communicate with external electronic and/or computational components. The first signaling interface 2408 operates to communicate with the administration computer 2304 over communication link 2308a, as described above. The second signaling interface 2412 operates to communicate with the various electronic components associated with the cleaning station 100a including the RFID reader 220 and the optical sensor 224. The second signaling interface 2412 may be a portion of a backplane incorporated into cleaning station 100a that includes a connection to the cleaning station's 100a electronic components. Alternatively, if the cleaning station operations monitor 228 is implemented as a stand-alone computer, the cleaning station operations monitor 228 may communicate with the cleaning station's electronic components through a network or serial bus connection.

The memory 2404 may include a plurality of stored program applications or modules that implement various features of a compliance monitoring system. In accordance with embodiments of the present invention, the memory 2404 may include a compliance monitoring module 2416 to verify the identity of a user 204 and whether the user maintains their hands in the cylinders 108 for a complete washing cycle. Additionally, the memory 2404 may include data structures 2432 associated with the various modules. In accordance with embodiments of the present invention, the data structures 2432 include a cleaning station-use record 2436 and one or more brush replacement records 2440.

In accordance with embodiments of the present invention, a brush replacement module 2428 may be provided to monitor whether a new brush is timely placed within the cleaning station 100a. The brush replacement module 2428 may provide a warning to a user, such as through a sensory perceptible warning device 236 (e.g, screen, light, speaker, vibrating device, etc.) that the brush needs to be replaced. The brush replacement module 2428 may be configured to deactivate the cleaning station 100a until a new and acceptable brush is replaced, as evidenced by the RFID reader 220 identifying a brush RFID tag 400 of a brush that has not been previously used. The brush replacement module 2428 may be configured to monitor installation of a new brush, and/or removal and reinstallation of an existing brush that has been sanitized.

Alternative and/or in addition to a brush replacement module 2428, the cleaning station operations monitor 228 may include a consumables authentication module 2424 to monitor whether proper cleaning fluids and disinfectants are being used in the cleaning station 100. Such consumables may include a brush disinfectant that is used to maintain the sanitation of the brush should the brush be a non-disposable type of brush, or should disposable brushes also include a preferred disinfectant to maintain their sanitation during the period of their limited use. Accordingly, the cleaning station operations monitor 228 may be used with RFID reader 220 or with another RFID reader to monitor whether proper brush disinfectants and other consumable products are authorized for use within the cleaning station 100, and to further monitor the levels of such materials.

An exemplary cleaning station-use record 2436 having data associated with a plurality of users 204 is shown in FIG. 25. In accordance with embodiments of the present invention, an entry in the cleaning station-use record 2436 may include an employee name 2500 indicating who used the cleaning station 100a, a time stamp 2504 indicating when the cleaning cycle was initiated, a duration 2508 indicating how long the user 2504 kept his or her hands in the cylinder 108, the date 2512, whether use was performed with a proper brush in place 2516, and a compliance indicator 2520 specifying whether or not the user 204 kept his or her hands in the cylinder 108 for the required time with a proper brush in place. As an example, the station-use record shown in FIG. 25 indicates that on May 21, 2006 Janet Smith did not meet the hand-washing requirement because at 8:00.00 A.M. the unit would not operate because the brush status was not acceptable. After the brush was replaced, others met the hand-washing requirement. Such a report allows a facility the ability to track employee activities when an attempted cleaning station use fails, and to determine and/or document whether alternative hand hygiene methods were used when the cleaning station was inoperative because of the necessity to replace the brush.

In an alternative embodiment, the cleaning station-use record 2436 may contain only raw data such as the time 2504, date 2512 and duration 2508 of the cleaning cycle while determinations related to compliance requirements are made separately, such as by a separate module running on the administration computer 2304.

Referring now to FIG. 26, a brush replacement record 2440 is shown. Here, the record includes data associated with whether the brush was timely replaced for a given date for a given cleaning station. In accordance with embodiments of the present invention, an entry in the brush replacement record 2440 may include a cleaning station designation 2600, the date 2604, and a proper brush compliance indicator 2608 specifying whether or not a proper brush was in-place on the associated date. Such records can be customized to include additional data, such as the time the brush was replaced, the person who replaced the brush, etc.

Figure 27:
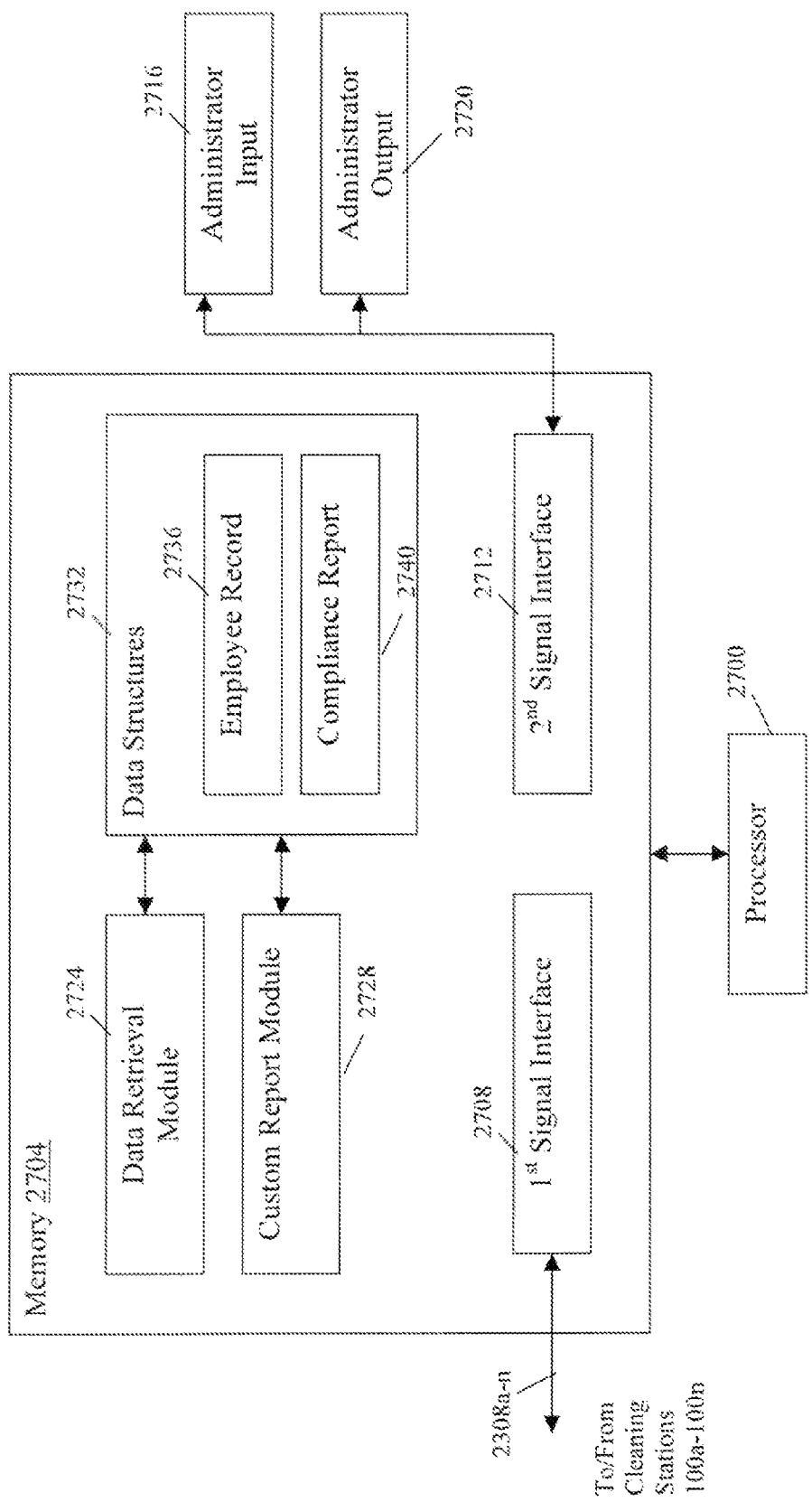
FIG. 27 is a block diagram of an administration computer in accordance with embodiments of the present invention.

Referring now to FIG. 27, a block diagram showing components and features of the administration computer 2304 is illustrated. Administration computer 2304 includes a processor 2700, a memory 2704 and signaling interfaces 2708 and 2712 operable to communicate with external electronic and/or computational components. The first signaling interface 2708 operates to communicate with the cleaning stations 100a-100n over communication links 2308a-2308n, as described above. The second signaling interface operates to communicate with the various input 2716 and output 2720 devices associated with the administration computer 2304.

The input device 2716 may be, for example, a keyboard or a mouse. The output device 2720 may be, for example, a monitor or a printer.

The memory 2704 includes a plurality of stored program applications or modules that implement various features of a compliance monitoring system. In accordance with embodiments of the present invention, the memory 2704 may include a data retrieval module 2724 and a custom report module 2728. Additionally, the memory 2704 may include data structures 2732 associated with the various modules. In accordance with embodiments of the present invention, the data structures 2732 may include an employee record 2736 and/or a compliance report 2740.

The data retrieval module 2724 operates to retrieve data associated with cleaning stations 100a-100n. Such data may include data related to cleaning station usage and/or brush maintenance data. The data may be contained in a cleaning station-use record 2436 and/or a brush replacement record 2340 associated with a cleaning station 100a-100n. Additionally, the data retrieval module 2724 may operate to maintain an employee record.

The custom report module 2728 operates to generate the compliance report 2740. The compliance report is generated from data contained in each station-use record 2436 associated with cleaning stations 100a-100n. An exemplary compliance report is shown in FIG. 28. In accordance with embodiments of the present invention, an entry in the compliance report 2740 may include an employee name 2800, time stamp 2804 indicating when a cleaning cycle was initiated, the date 2808 of the cleaning cycle, the station designation 2812 where the cleaning cycle took place, a brush compliance indicator 2814 specifying whether or not the status of the brush was acceptable, and a compliance indicator 2816 specifying whether or not the user 204 met the compliance requirement. As an example, the compliance report shown in FIG. 28 indicates that on May 21, 2006 Janet Smith did not meet the hand-washing requirement attempted at 8:00.00 A.M at cleaning station A. As noted, compliance reports may include data pertaining to user statistics. Alternatively, or in addition to reports comprising user statistics, reports may be generated that are directed to the consumables, such as soap and disinfectants.

Figure 29:
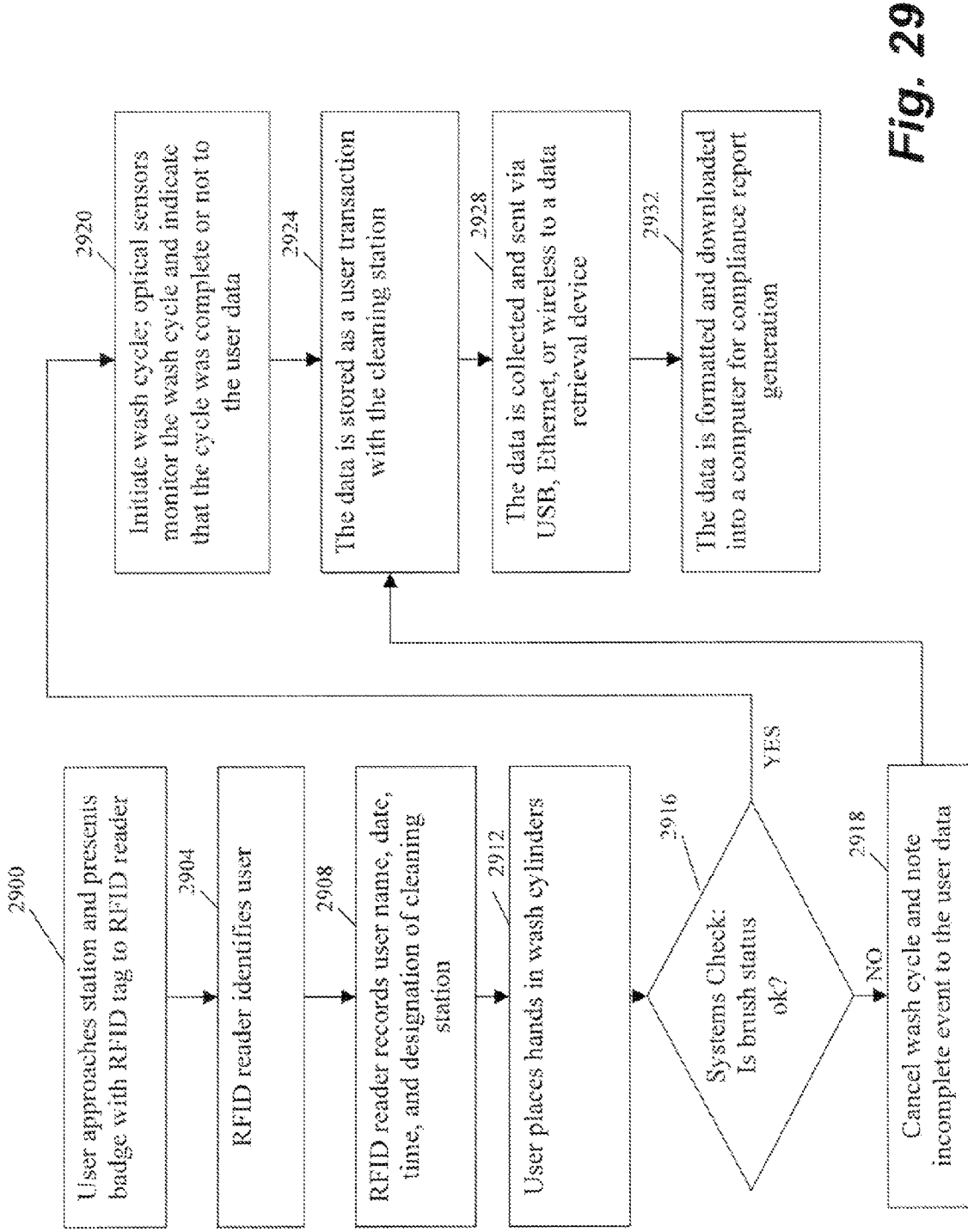
FIG. 29 is a flow chart depicting aspects of a method of monitoring hand-washing compliance in accordance with embodiments of the present invention. The drawings are not necessarily to scale.

In accordance with embodiments of the present invention, FIG. 29 shows a block diagram illustrating the steps of a method of monitoring a compliance requirement including a check for the brush status. Initially, at step 2900 a user 204 approaches a cleaning station 100a and presents a badge having a RFID tag 232 to an RFID reader 220. At step 2904 the RFID tag 232 is read and the user 204 is identified. At step 2908 the user's 204 name, the date, the time, and the designation of the cleaning station 100a are recorded. At step 2912 the user 204 places her or his hands in position to be washed. At step 2916 a system check is performed, including checking if the brush status is okay, such as by cross-checking the date and/or time the brush RFID tag 400 was initially read against the allowed time for a particular brush to be authorized for use within the cleaning station. If the brush status is okay, at step 2920 the wash cycle is initiated and completed and data is recorded including the duration of time the user 204 allowed his or her hands to be washed. At step 2924 the transaction is completed and recorded. If the systems check at step 2916 fails, then the wash cycle is cancelled at step 2918. Here, the user is preferably advised by the cleaning station 100, such as via a message or warning through warning device 236, that the cleaning station is not operative, and advised to wash their hands elsewhere. Step 2920 is then skipped, and at step 2924 the transaction is completed and recorded. At step 2928 data is collected from the cleaning stations 100a-100n over the communication links 2308a-2308n. Finally, at step 2932 the collected data is used to generate a compliance report 2740. Additional steps associated with the method may include: monitoring proper maintenance of brush component, and/or monitoring the application of a sanitizer or disinfectant to maintain the sanitation of a brush component.

The following U.S. patents are incorporated herein by reference in their entirety: U.S. Pat. Nos. 5,823,447, 5,265,628; 4,817,651; and 4,925,495.

The present invention, in various embodiments, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover, though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An automated appendage cleaning system for removing at least one of a particulate, chemical, and biological substance from an appendage of a user, comprising:
 a cleaning station comprising an automatic washing mechanism for cleaning at least one appendage of a user; and
 a friction enhancing structure operatively interconnected to the cleaning station, the friction enhancing structure comprising an electronic identifying device, wherein the electronic identifying device provides a designation data of the friction enhancing structure;

a sensor operable to sense placement of the appendage of the user in spatial proximity to the friction enhancing structure of the cleaning system;

a compliance monitoring module operable to determine a length of time that the appendage was positioned in spatial proximity to the friction enhancing structure; and a brush replacement module operable to determine that the friction enhancing structure associated with the designation data requires replacement and/or disinfecting in response to passage of a selected time duration of use;

wherein the electronic identifying device is in communication with an automated reader, wherein the automated reader is configured to perform at least one of interrogating, scanning, and receiving a signal from the electronic identifying device for obtaining the designation data.

2. The system of claim 1, wherein the electronic identifying device comprises an RFID tag and the automated reader is an RFID reader and wherein the designation data is a unique RFID tag identifying the friction enhancing structure.

3. The system of claim 1, wherein the friction enhancing structure is selected from the group consisting of a brush, pad, sponge, and non-fluid tactilely perceptible material and wherein the duration of use is a function of the length of time that the appendage is positioned in spatial proximity to the friction enhancing structure.

4. The system of claim 1, wherein the automatic washing mechanism includes a recessed portion comprising an inner wall, and wherein the friction enhancing structure is located radially interior of the inner wall.

5. The system of claim 4, wherein the friction enhancing structure is detachably connected to the inner wall.

6. The system of claim 4, wherein the friction enhancing structure is mounted proximate a distal end of the recessed portion.

7. The system of claim 4, wherein the recessed portion comprises at least one nozzle, and wherein the nozzle projects at least one of a cleaning fluid and water toward the appendage.

8. The system of claim 7, wherein the nozzle comprises an orifice for projecting a stream pattern and not a diffused spray or planar spray pattern.

9. The system of claim 4, wherein the recessed portion comprises a cylinder and wherein the length of time that the appendage is positioned in spatial proximity to the friction enhancing structure is determined by the length of time that the sensor senses that an optical signal is broken.

10. The system of claim 9, wherein cylinder is rotatable and wherein the length of time that the appendage is positioned in spatial proximity to the friction enhancing structure is determined by the length of time that the sensor senses that an optical signal is broken.

11. The system of claim 9, wherein the optical signal is broken when the user positions the appendage within a washing mechanism of the cleaning system, and wherein the optical signal is restored when the user removes the appendage from the washing mechanism of the cleaning system, and wherein the length of time that the appendage is positioned in spatial proximity to the friction enhancing structure is determined by the length of time that the sensor senses that the optical signal is broken.

12. The system of claim 1, further comprising an administration computer operable to communicate with the automated reader to obtain the designation data.

13. The system of claim 12, wherein the administration computer comprises a tracking algorithm for monitoring at least one of (a) a statistic concerning the friction enhancing device, and (b) the designation data.

* * * * *